(12) United States Patent
Babcock et al.

(10) Patent No.: US 9,569,858 B2
(45) Date of Patent: Feb. 14, 2017

(54) CLOUD-BASED SYSTEM FOR WATER ANALYSIS

(71) Applicants: James Bennett Babcock, Phoenix, MD (US); Rebecca Elizabeth Petruccy, Baltimore, MD (US); Bretton Wade, Baltimore, MD (US); Dominic Kennedy, Yowie Bay (AU)

(72) Inventors: James Bennett Babcock, Phoenix, MD (US); Rebecca Elizabeth Petruccy, Baltimore, MD (US); Bretton Wade, Baltimore, MD (US); Dominic Kennedy, Yowie Bay (AU)

(*) Notice: Subject to any disclaimer, the term of this patent is extended or adjusted under 35 U.S.C. 154(b) by 0 days.

(21) Appl. No.: 14/622,282

(22) Filed: Feb. 13, 2015

(65) Prior Publication Data

US 2015/0310634 A1 Oct. 29, 2015

Related U.S. Application Data

(60) Provisional application No. 61/939,509, filed on Feb. 13, 2014.

(51) Int. Cl.
*G06K 9/00* (2006.01)
*G06T 7/40* (2006.01)
(Continued)

(52) U.S. Cl.
CPC ........... *G06T 7/408* (2013.01); *G01N 21/78* (2013.01); *G01N 33/18* (2013.01); *G01N 21/274* (2013.01);
(Continued)

(58) Field of Classification Search
CPC ....... G06K 9/228; G06K 9/4652; G06T 7/408; G06T 2207/10024; G06T 2207/30108; H04N 17/02; G06F 19/3406; G06F 19/3418; G06F 19/366; G06Q 50/22; G06Q 50/24; G01N 21/01; G01N 21/25; G01N 21/253; G01N 21/27; G01N 21/274; G01N 21/474; G01N 21/77; G01N 21/78; G01N 21/8483; G01N 31/00; G01N 31/22; G01N 33/18; G01N 33/50; G01N 33/66; G01N 33/92; G01N 35/00; G01N 2001/027; G01N 2021/177; G01N 2035/00108; G01N 2035/00326; G01N 2035/00495; G01N 2201/0221; G01N 2201/0222; G01N 2021/7759; A61B 5/0077; A61B 5/14532; A61B 5/411; A61B 5/44; A61B 5/6898; A61B 5/743; A61B 10/0045; A61B 2562/0295; G01J 3/02; G01J 3/0272; G01J 3/0264; G01J 3/0291; G01J 3/10; G01J 3/46; G01J 3/462; G01J 3/50; G01J 3/524; G01J 2203/466; G01J 2003/466; Y10S 435/97; Y10T 436/11; Y10T 436/144444; Y10T 436/2575; G09G 3/2003; G09G 3/3611; G09G 2320/0242; G09G 2320/0666; G09G 2320/145; G09G 2340/145

See application file for complete search history.

(56) References Cited

U.S. PATENT DOCUMENTS 5,408,535 A 4/1995 Howard, III et al.
6,285,454 B1 9/2001 Douglas et al.
(Continued)

*Primary Examiner* — Jose Couso
(74) *Attorney, Agent, or Firm* — Ober, Kaler, Grimes & Shriver; Royal W. Craig

(57) ABSTRACT

A cross-platform web-based system for water testing capable of measuring, analyzing and maintaining the quality of water using a plurality of different test strip readers each configured to obtain a digital image of a reagent test strip, normalize and analyze color information in the digital image by colorimetric analysis, and to transmit a set of colorimetric
(Continued)

values corresponding to said digital image to a cross-platform cloud-based system for analysis. The cloud-based server(s) receive the colorimetric values, calculate analyte parts-per-million (ppm), and return the calculated analyte ppm with consistant results no matter which reader is used.

20 Claims, 14 Drawing Sheets

(51) Int. Cl.
   *G01N 33/18* (2006.01)
   *G01N 21/78* (2006.01)
   *G01N 21/27* (2006.01)
   *G01N 21/77* (2006.01)
(52) U.S. Cl.
   CPC .............. *G01N 2021/7759* (2013.01); *G06T 2207/10024* (2013.01); *G06T 2207/30108* (2013.01)

(56) References Cited

U.S. PATENT DOCUMENTS

| | | | |
|---|---|---|---|
| 6,614,530 | B1 | 9/2003 | Duez et al. |
| 7,041,468 | B2 | 5/2006 | Drucker et al. |
| 7,262,779 | B1 | 8/2007 | Sones |
| 7,339,673 | B2 | 3/2008 | Roman |
| 7,885,444 | B2 | 2/2011 | Wang |
| 8,142,722 | B2 | 3/2012 | Morris et al. |
| 8,145,431 | B2 | 3/2012 | Kloepfer et al. |
| 8,435,738 | B2 * | 5/2013 | Holmes ............. G01N 33/50 422/68.1 |
| 2007/0242064 | A1 | 10/2007 | Kuo |
| 2008/0034845 | A1 | 2/2008 | Morris et al. |
| 2010/0045789 | A1 | 2/2010 | Fleming et al. |
| 2010/0254581 | A1 | 10/2010 | Neeser et al. |
| 2011/0275162 | A1 | 11/2011 | Xie et al. |
| 2012/0063652 | A1 | 3/2012 | Chen et al. |

\* cited by examiner

D

E

F

G

Pool Water 02-Jul-2013 am

Test Results

| Free Chlorine | 2-4 ppm | 0 | ppm |
| --- | --- | --- | --- |
| pH | 7.4 - 7.8 | 8.1 | ppm |
| Alkalinity | 80 - 120 ppm | 80 | ppm |
| Hardness | 200 - 400 ppm | 800 | ppm |
| Cyanuric acid | 30 - 50 ppm | 0 | ppm |

Describe Water Conditions - click all that apply

| Bather Comfort | ☐ Eye / Skin Irritation | ☐ Water Smells Like Chlorine | | |
| --- | --- | --- | --- | --- |
| Visible Algae | ○ Green Haze | ○ Green-Black Spots | ○ Yellow-Brown Patches | ○ Pink Same |
| Water Clarity | ☐ Cloudy / Hazy | ☐ Dirty / Muddy | | |
| Water Color | ○ Green | ○ Blue-Green | ○ Purple | ○ Brown |
| Surface Stains | ○ Blue Green | ○ Rust-Brown / Yellow-Brown | ○ Black-Brown | ○ Gray |
| Surface Problems | ☐ Corrosion | ☐ Scale Along Waterline | ☐ Oily Ring Along Waterline | ☐ Water Foaming |

[ Fetch Water Analysis Report ]

Fig. 9 (cont)

CLOUD-BASED SYSTEM FOR WATER ANALYSIS

CROSS-REFERENCE TO RELATED APPLICATION(S)

The present application derives priority from U.S. provisional application 61/939,509 filed 13 Feb. 2014.

BACKGROUND OF THE INVENTION

1. Field of the Invention

The present invention relates generally to water testing systems, and more specifically, to a cross-platform web-based system for water testing capable of measuring, analyzing and maintaining the quality of water using a plurality of different test strip readers.

2. Description of the Background

Water quality is important in a variety of industries. For example, pool maintenance requires periodic regular testing of pool water and careful maintenance by chemical additives. Testing and balancing swimming pool water can be a difficult process for the owner. There are myriad test kits available with different capabilities. At minimum a suitable test kit will test for available chlorine, cyanuric acid, pH, total alkalinity, and calcium hardness. Depending on the test results the foregoing may need to be balanced. Both testing and balancing can be fraught with error and frustration.

Reagent test strips are the most common testing modality. Water test strips usually have a plurality of reagent test areas, each test area undergoing a color change in response to contact with a particular chemical constituent. The presence and concentrations of these constituents of interest can be determined by a colorimetric analysis of the color changes undergone by the test strip. Usually, this analysis involves a color comparison between the test area or test pad and a color standard or scale.

A variety of conventional test strip reading instruments exist which can determine the color change of a test strip. However, different readers employ different imagers, sample trays, differences in background lighting, different CCDs, lenses and the like, any or all of which can produce vastly different color information for the same test strip.

U.S. Pat. No. 6,614,530 to Duez et al. (Biophotonics S.A.) issued Sep. 2, 2003 shows a method for the colorimetric measurement of a defined region on an image using a color camera, and discloses color-correction of tristimulus (R, G, B) values by selection of an area within an image in order to correct the imperfection in the homogeneity of the sensor and of the illuminant.

U.S. Pat. No. 5,408,535 to Howard, III et al. (Miles, Inc.) issued Apr. 18, 1995 shows a video test strip reader for evaluating test strips that uses a video imager or camera. The reader is connectable to a computer which choreographs imaging at the proper times and calculates the test results, such as the concentration of the constituents of interest.

United States Patent Application 20120063652 to Chen et al. (Teco Diagnostics) published Mar. 15, 2012 shows a method and apparatus for color-based reaction testing of biological materials by capturing, in an uncalibrated environment, a digital image of an exposed test strip, together with an adjacently-located reference color chart or on-strip color chart. The image data specifically representing the individual test pads on the test strip, as well as the reference color blocks on the reference chart, are then located within the captured image, and compared to identify any color matches. The claims require capturing a digital image of an exposed test strip and a reference color chart in an uncalibrated environment.

U.S. Pat. No. 7,885,444 to Wang (Transpacific Systems, LLC) issued Feb. 8, 2011 shows a method for determining a response of each probe zone on a test strip by establishing a plurality of target scan lines through the pads and one "white" control line adjacent the pads, and using the white line as a reference for determining a color response of the target lines.

United States Patent Application 20100045789 by Fleming et al. published Feb. 25, 2010 shows an assay system for test strips which looks for "control" signal line(s) on the strips and conducts an assay evaluation based at least on the control signal lines.

United States Patent Application 20080034845 by Morris (Hach Co.) published Feb. 14, 2008 shows an electronic device for analyzing an aqueous solution with a housing configured to receive a test strip.

U.S. Pat. No. 6,285,454 to Douglas et al. (Mercury Diagnostics, Inc.) issued Sep. 4, 2001 shows an assay system that accurately docks a removable test strip with an optics system including an illumination LED and photodetector.

U.S. Pat. No. 8,142,722 to Morris et al. (Hach Co.) issued Mar. 27, 2012 shows a handheld portable electronic test strip tester.

U.S. Pat. No. 7,339,673 to Roman (Siemens Healthcare) issued Mar. 4, 2008 shows a miniature readhead for a photometric test strip reader.

U.S. Pat. No. 7,041,468 to Drucker et al. (TheraSense, Inc.) issued May 9, 2006 shows a blood glucose test strip receptacle for connection to a hand-held computer.

U.S. Pat. No. 8,145,431 to Kloepfer et al. (Advanced Medical Products GmbH) issued Mar. 27, 2012 shows a smart-phone-based body fluid test strip positioner. The test strip positioner positions a test strip in the FOV of the phone's camera lens to permit the camera to capture an image. A light source disposed within the positioner illuminates the analyte containing test strip to facilitate the capture of the image of the test strip. Software in the smart phone performs quantitative analysis.

United States Patent Application 20100254581 by Neeser et al. (Reveal Sciences) published Oct. 7, 2010 shows a method and apparatus for analyzing samples by obtaining an image using any mobile consumer device, storing and transmitting the image to a remote server, analyzing the image using an analysis software on a remote server, and sending the results of the analysis back to the consumer device.

U.S. Pat. No. 7,262,779 to Sones (Applied Vision Company, LLC) issued Aug. 28, 2007 shows a differential imaging colorimeter which utilizes a RGB color camera to provide accurate differential colorimetry.

United States Patent Application 20070242064 by Kuo (Asustek Computer Inc.) published Oct. 18, 2007 shows a camera used as a colorimeter and ambient light sensor.

United States Patent Application 20110275162 by Xie et al. (Alverix, Inc.) published Nov. 10, 2011 shows a low-cost assay test strip reader in which the strip is placed in a shuffle that moves it past a photodetector, which detects an optical signal at a single point. The movement of the test strip with respect to the detector allows it to scan a length of the test strip.

The foregoing references tend to rely on a fixed reference standard placed in the field of view of the camera for calibration. A fixed reference standard is not a workable solution for a cross-platform web-based system with multiple different test strip readers, all with different imaging characteristics. What is needed is a way to integrate and calibrate multiple different test strip reader types in a cross-platform cloud-based system for water testing capable of measuring, analyzing and maintaining the quality of water using any of the various test strip readers, and to obtain consistent results no matter the reader used.

DETAILED DESCRIPTION OF THE PREFERRED EMBODIMENTS

The present invention is a cloud-based colorimetric water analysis system that includes a computer-based combination of software and accessory hardware to make it possible for users to analyze pool water, for example, using any of a combination of portable test strip imaging devices including a computerized smartphone such as an iPhone®, web-enabled computer, dedicated in-store kiosk, or computer-peripheral digital strip reader (DSR). Each of these test strip reader devices communicates with a cloud-based computer system for transmitting imaging results and receiving analysis results therefrom.

For all of the test strip reader devices local software provides a user interface to facilitate taking a photo of a reagent test strip using an on-board camera system (or recall of a stored image). The software normalizes and then analyzes the color information in the image and provides an immediate colorimetric analysis and treatment recommendations.

The local software seamlessly interfaces with the camera software to target a new image, automatically correlating multiple test pads on each strip to the multiple reagents being tested. However, the user interface allows user-confirmation and adjustment at each automated step. For example, the user interface allows user-adjustment from software-selected test strip areas and colors based on visual appearance.

Rather than transmitting the entire image, just the colorimetric values for each test strip patch are transmitted from the local computer to a cloud-based computer system for analysis. Cloud-based software receives the final color selections from any of the various test strip readers, which selections are analyzed for analyte ppm by reference to a lookup table. For the above-referenced DSR this analysis entails a RGB to LAB color data conversion, as calibrations and comparisons are run with LAB color data. Otherwise, RGB is used. The software correlates the test results to analysis and treatment recommendations, which are returned and displayed in real time.

Figure 1:
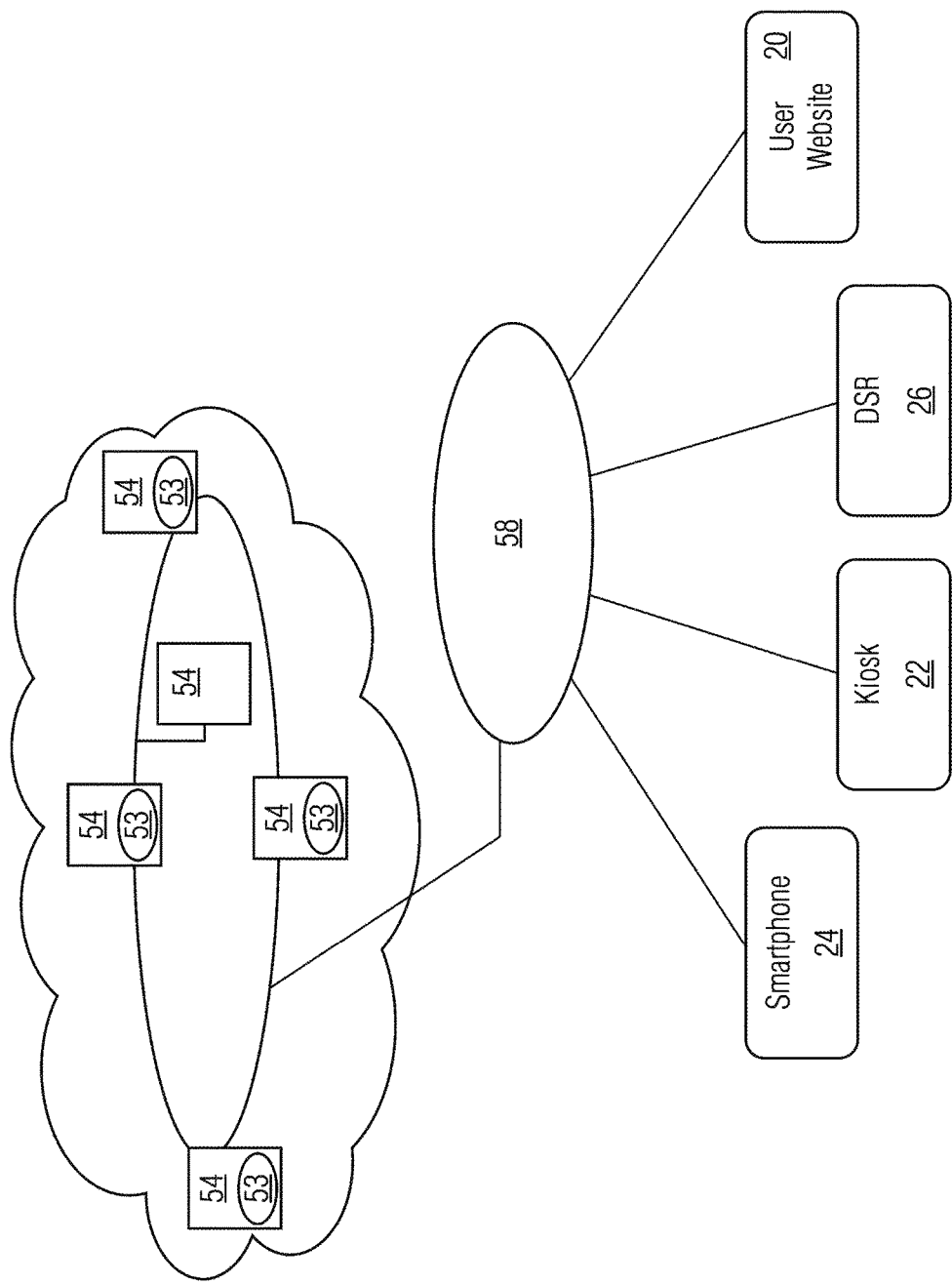
FIG. 1 illustrates a suitable cloud computing network 50 according to the invention.

FIG. 1 illustrates a suitable cloud computing network 50 with an attached cloud data store 52. Any number of cloud computing nodes 54 may be connected in the cloud computing network 50, each running cloud computing services 53 in accordance with the present invention.

A local network 58 is in communication with the cloud computing network 50. End users in local network 58 access cloud-based applications 53 from any of a combination of portable test strip reader devices in accordance with the invention, including any computerized smart device such as an iPhone® 24, any web-enabled computer 20, dedicated in store kiosks 22, or digital strip readers (DSRs) 26, all as will be described.

Each test strip reader device 20, 22, 24, 26 accesses cloud computing services 53 through a web browser or a lightweight desktop or mobile application, using a standard I/O-devices such as a keyboard and a computer screen. Each test strip reader device 20, 22, 24, 26 takes a TIFF-format photo of a standard 6-way test strip, and locally calibrates, corrects and computes the RGB color values for each patch on the strip. Data representing the corrected RGB color values is sent to the cloud computing network 50. Once uploaded, the collective data is subjected to an analysis process described below, and results and treatment recommendations are transmitted back to the user locally.

Test Kit

Figure 2:
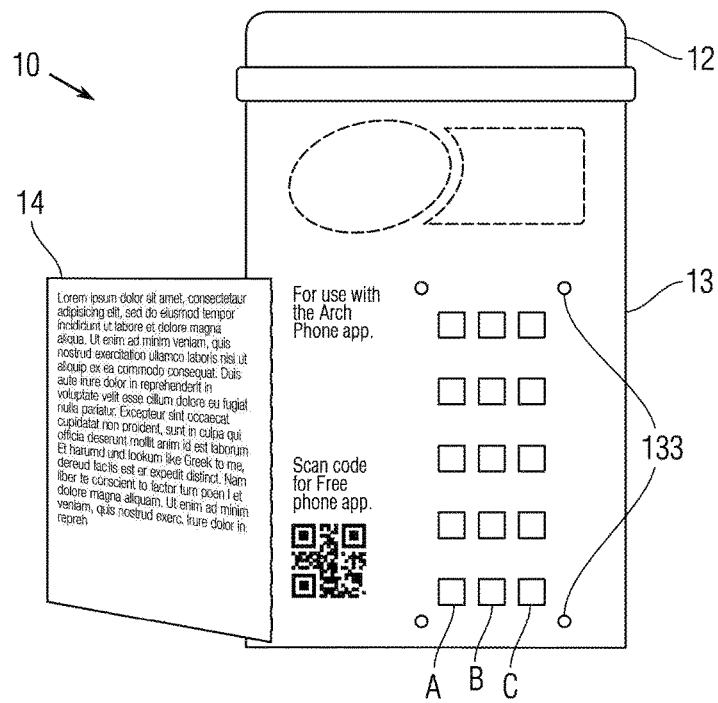
FIGS. 2-3 are a front and back view, respectively, of an exemplary test kit 10 suitable for use with the present invention.
Figure 3:
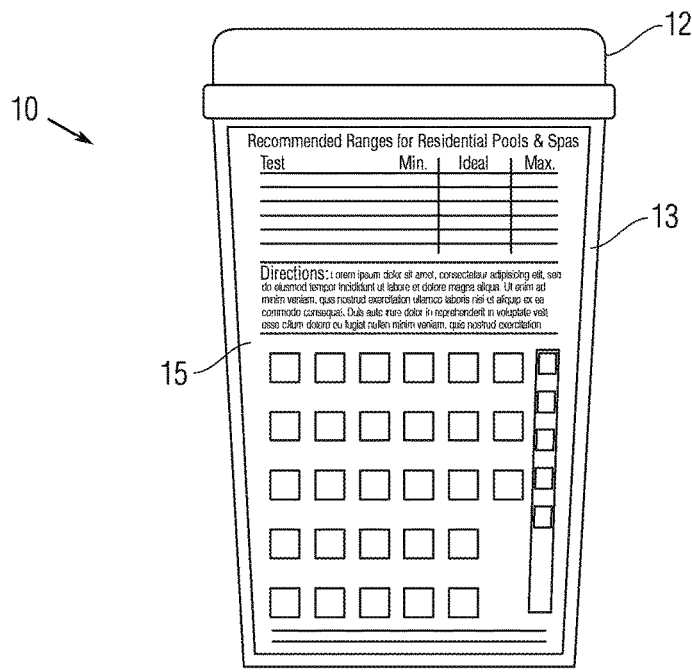

FIGS. 2-3 are a front and back view, respectively, of an exemplary test kit 10 suitable for use with the present invention. Test kit 10 generally comprises a two-section trapezoidal housing including a cover 12 snap-fit onto a base 13. A peel-away bifold label 14 is adhered to the front of the base and folds out to reveal instructions and a QR code link for downloading the smartphone 24 application to be described, and also a template for attaching and centering a test strip for imaging vis-à-vis the smartphone 24 and imaging software downloaded thereto. Marketing information relevant to accessing the dedicated in store kiosks 22, or digital strip readers (DSRs) 26 and instructions therefor appears on the fold-out portion of label 14. As seen in FIG. 3 the backside of base 13 also contains label 15 adhered thereto and displaying (at top) recommended ranges for available chlorine, cyanuric acid, pH, total alkalinity, and calcium hardness. Directions for using the test kit are printed below, and a visual color matching scale appears there beneath for visually ascertaining the test results from the test strip, based on a visual comparison of test strip patches (denoted at right) to reagent colors and corresponding concentrations (at left).

Test kit 10 encloses a turn-key test solution suitable for standalone manual testing (using label 15) and/or semi-automated testing when used with any of the test strip reader device 20, 22, 24, 26 and cloud computing services 53.

Figure 4:
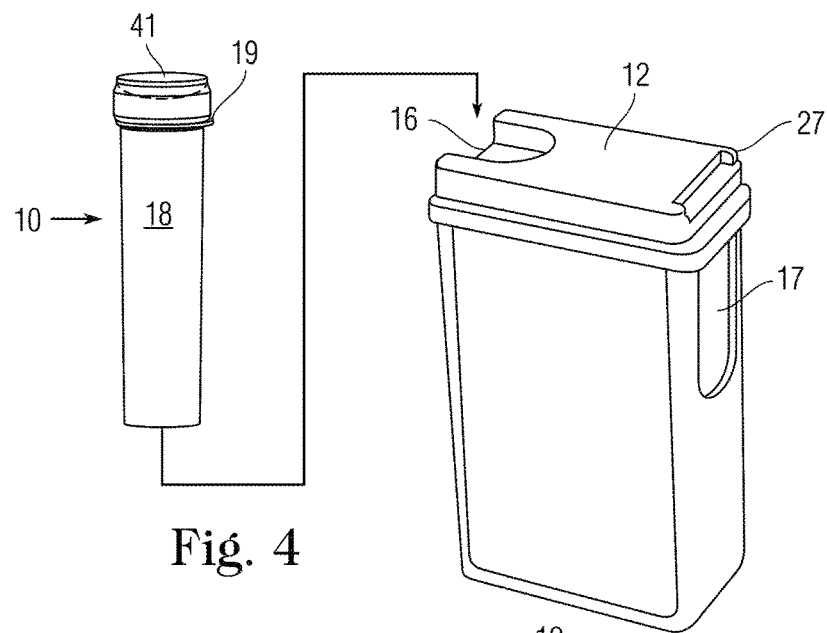
FIG. 4 is a perspective view of the test kit 10.

As seen in FIG. 4, the test kit 10 is formed with cover 12 that snaps-fit atop a base 13. The cover 12 is formed with a slightly frusto-conical open-ended bay 16 protruding downward. With cover 12 fit atop the base 13 the bay 16 runs from the top left partway to the bottom of base 13 for seating a sample vial 18. The sample vial 18 comprises a slightly frusto-conical plastic holder and concave cap 41 attached by plastic hinge. The slight frusto-conical shape allows the vial 18 to slide easily into conforming bay 16, guided therein into position, and to seat flush for ease of access and stowage. Preferably, a detent tab 19 is formed at the mouth of vial 18 and corresponding notch formed in the mouth of bay 16 to releasably lock vial 18 in place once fully inserted. The vial 18 is compression-fitted with a concave "displacement" cap 41 as seen in FIG. 4. The cap 41 conforms to the neck of vial 18 and is inserted therein to the limit of its flange. In use, the vial 18 is removed, uncapped, dipped into pool water, and recapped to contain a sample of the water. Vial 18 may be conveniently restowed inside bay 16 with water sample intact for transport. The concavity of cap 41 displaces some of the volume of vial 18 to guard against overfilling with a water sample, and removes air in the vial to prevent dissipation of chlorine in the sample. This ensures that when the cap 41 is removed from vial 18 to dip a test strip, no spillage occurs.

Figure 5:
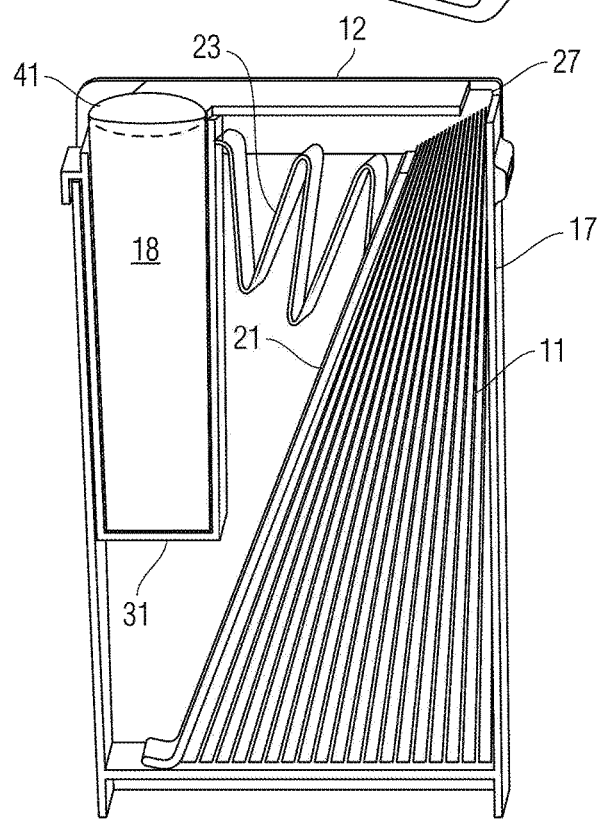
FIG. 5 is a cross-section of FIG. 5.

As seen in the cross-section of FIG. 5 a supply of test strips 11 are provided, each individually packed inside a wrapping for ease of removal. The individual test strip supply 11 is biased against the far side of base 13 by a spring-damper which comprises a flat member 21 and an extended accordion-style spring arm 23 which bears against the far side of base 13 to maintain compression on the test strips 11. The spring-arm may be an integrally molded resilient-plastic component, and is held in place by insertion of the distal end of spring-arm 23 into a notch in the underside of cover 12. The test strips 11 are biased against an elongate ejection aperture 17 through the side wall of base 13, which aperture 17 allows ejection of the abutting test strip 11 by an upward swipe of the user's thumb or finger. The user engages the midsection of the most proximate test strip 11 and presses against it with their thumb or finger, urging it upward through a slot 27 formed in the upper corner of the cover 12. This extends the top portion of the test strip outward through cover 12 where it may be easily retrieved by the consumer, fully withdrawn, and opened for use.

Given a water sample in vial 18, the consumer unwraps the test strip, dips it into the sample in vial 18 (in accordance with the timing instructions provided), and either adheres the test strip to the back of base 13 for visual or smartphone 24 testing or inserts the test strip in another test strip reader device 20, 22, 26 as described below.

In Store Kiosk 22

In accordance with the invention, an embodiment of the test strip reader comprises a semi-automated in-store kiosk 22 designed to automate consumer-interaction as much as possible such that consumers can purchase a test kit that holds thirty (30) strips, test their pool water at home, return to the store with test strip intact (in the kit), and perform reliable colorimetric analysis of their test strip vis-à-vis the in-store computerized in-store kiosk 22, which accepts and processes a test strip dipped into the sample.

Figure 6:
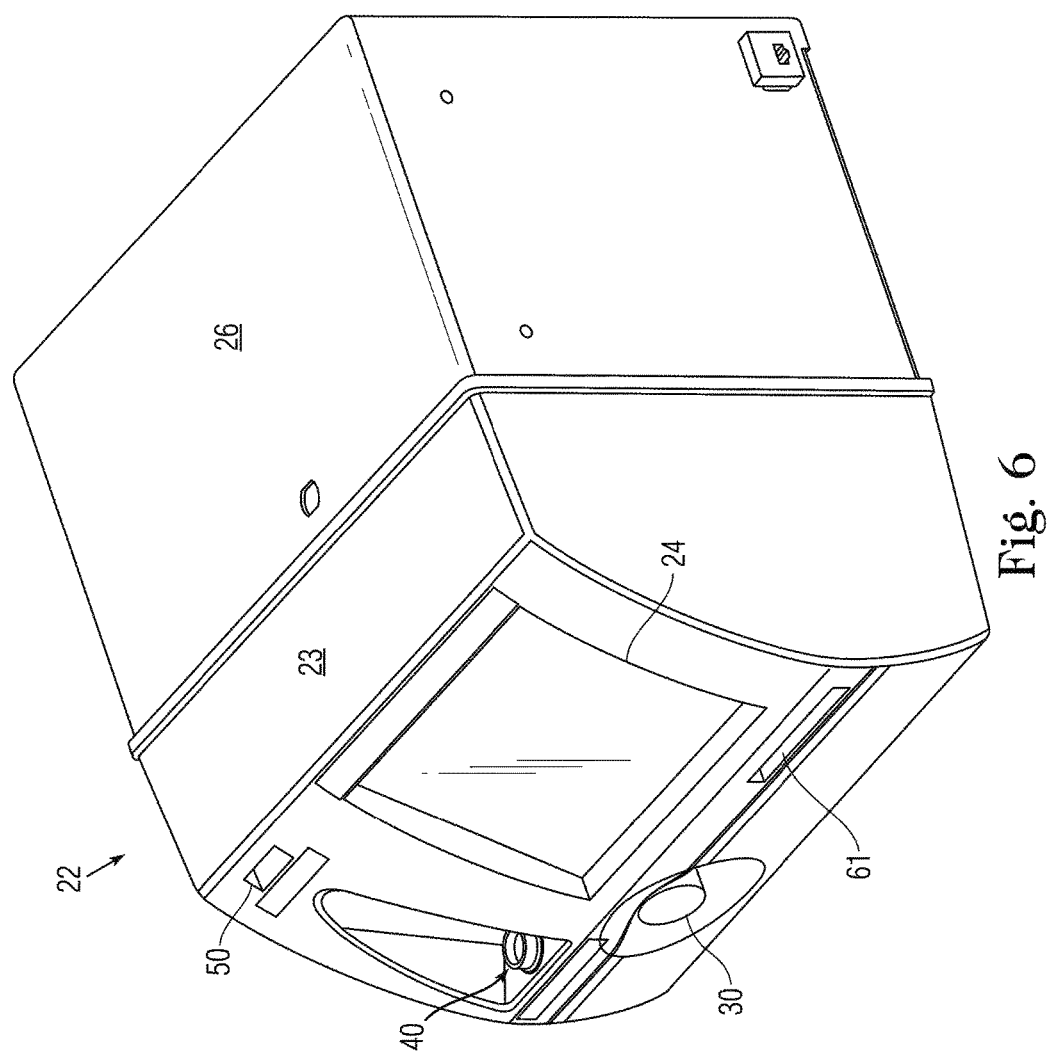
FIG. 6 illustrates an embodiment of the kiosk 22 in accordance with the invention.

FIG. 6 illustrates an embodiment of the kiosk 22 which generally includes a tabletop enclosure within which is housed an internal computer running a local software application that presents a graphical user-interface on frontally-visible panel-mounted display 24. The local software guides the consumer through the testing procedure.

Specifically, a consumer approaches the kiosk 22 with a water sample contained in a prescribed vial 18 (sold with the test kit 10 described above), and places the vial in a holding berth 40. They login the computerized in-store kiosk 22 and begin a guided series of steps for completing the testing process.

The consumer is instructed to unwrap a test strip (also provided with the test kit 10 described above), discard the wrapping foil in refuse slot 50, place the strip in the water in vial 18, and wait an appropriate time interval measured by a countdown. This ensures proper reaction development time.

The consumer is advised to eject the loading shuttle 30 by pressing on it ("Press Here"), which action ejects the shuttle to the loading position. The shuttle 30 is part of an internal imaging platform and ejection allows the user to mount the test strip therein. When the consumer places the test strip in the shuttle 30 and presses inward to reinsert it in the kiosk 22, the remainder of the imaging and analysis process is completed semi-automatically with an internal camera assembly 80 (to be described), and some optional input to the graphical user-interface. In the preferred embodiment the display 24, camera assembly 80 and internal computer are all parts of a conventional tablet computer (such as an iPad®) panel-mounted within a molded front panel 23 such that display 24 is visible as shown. The test results are displayed on display 24, and a test receipt with results and treatment recommendations is printed by an internal printer 60 (to be described) which receipt is dispensed through slot 61. The receipt indicates the proper chemicals and amounts to use, and store stock numbers for the appropriate chemicals, such that the consumer can take the receipt directly to a store clerk and acquire the appropriate chemical supply.

The housing generally comprises the molded front panel 23 (seen in FIG. 6) removably attached to an inner frame upon which the internal components (including iPad®) are mounted, and a five-sided rear enclosure 26 that slides over the inner frame on rail-brackets, joining the front panel 23.

Figure 7:
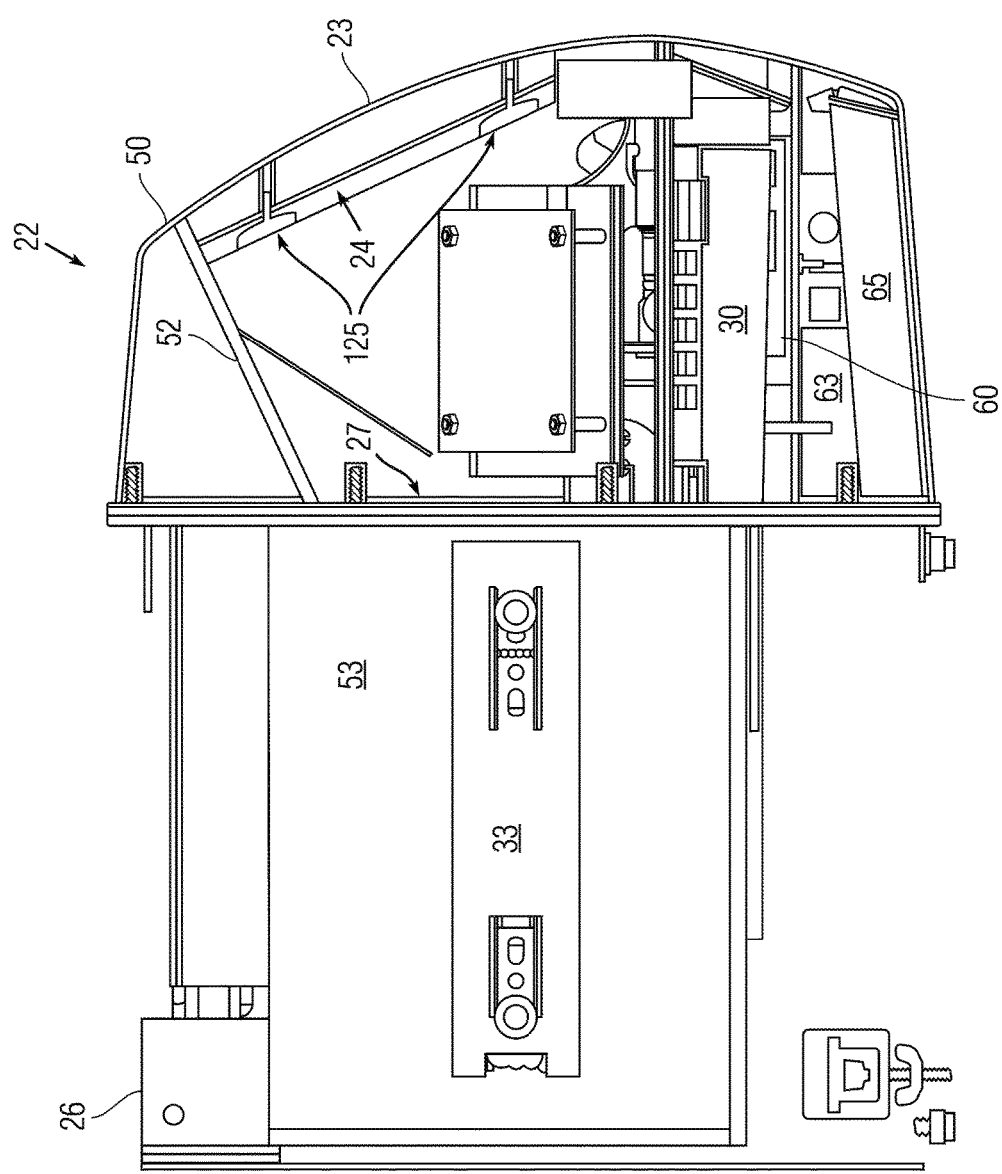
FIG. 7 illustrates kiosk 22 with housing 22 removed.

FIG. 7 illustrates kiosk 22 with front panel 23 and the rear housing 26 shaded to show the internal frame 27 upon which the operative components are mounted. Again, the computer and display 24 are combined in a touchscreen tablet here mounted by four corner brackets 125 to the front panel 23 for frontal display through front panel 23, and the tablet camera is used for taking images. A printer 60 is mounted proximate to tablet 24 (below and to the right) and is in wired or wireless communication there with. Printer 60 is preferably a conventional small-footprint thermal dot line roll tape printer, and in the preferred embodiment it is equipped with a Bluetooth transmitter for Bluetooth communication with printer 60. A dispenser roller is mounted behind the printer (obscured) for supporting a roll of thermal tape as it is fed into printer 60, and in the preferred embodiment a shroud is attached over the roll of tape, to the rear of printer 60 to protect the tape.

The refuse slot 50 continues down from the front panel 23 along an inclined feed tray 52 which empties into a refuse bin 53, enclosed within rear enclosure 26. There are two refuse bins 53 and 65, one upper 53 for receiving waste packaging from the unwrapped test strips inserted in slot 50 and one lower 65 for receiving the used test strips dumped from shuttle 30 after imaging is completed. Opposing rail-brackets 33 are mounted with one horizontally along refuse bin 53 and the other on bracket XX of inner frame 27, and a corresponding pair of rail-brackets are mounted sidelong internally of the rear enclosure 26 to allow the rear enclosure 26 to be slid onto the frame 27 to mate with front panel 23.

Preferably, the on-board camera of tablet 24 is used for imaging. Portable device cameras are typically color webcams. For example, where tablet 24 is an iPad® the camera is currently an iSight™ ¼-inch color CCD sensor with 640×480-pixel VGA resolution, with a custom-designed three-part F/2.8 lens with two aspherical elements. The camera is OEM-mounted to the rear of the tablet 24 and offers insufficient angle, magnification and lighting for present purposes, and so to improve these a lighting/magnification assembly 80 is provided.

Figure 8:
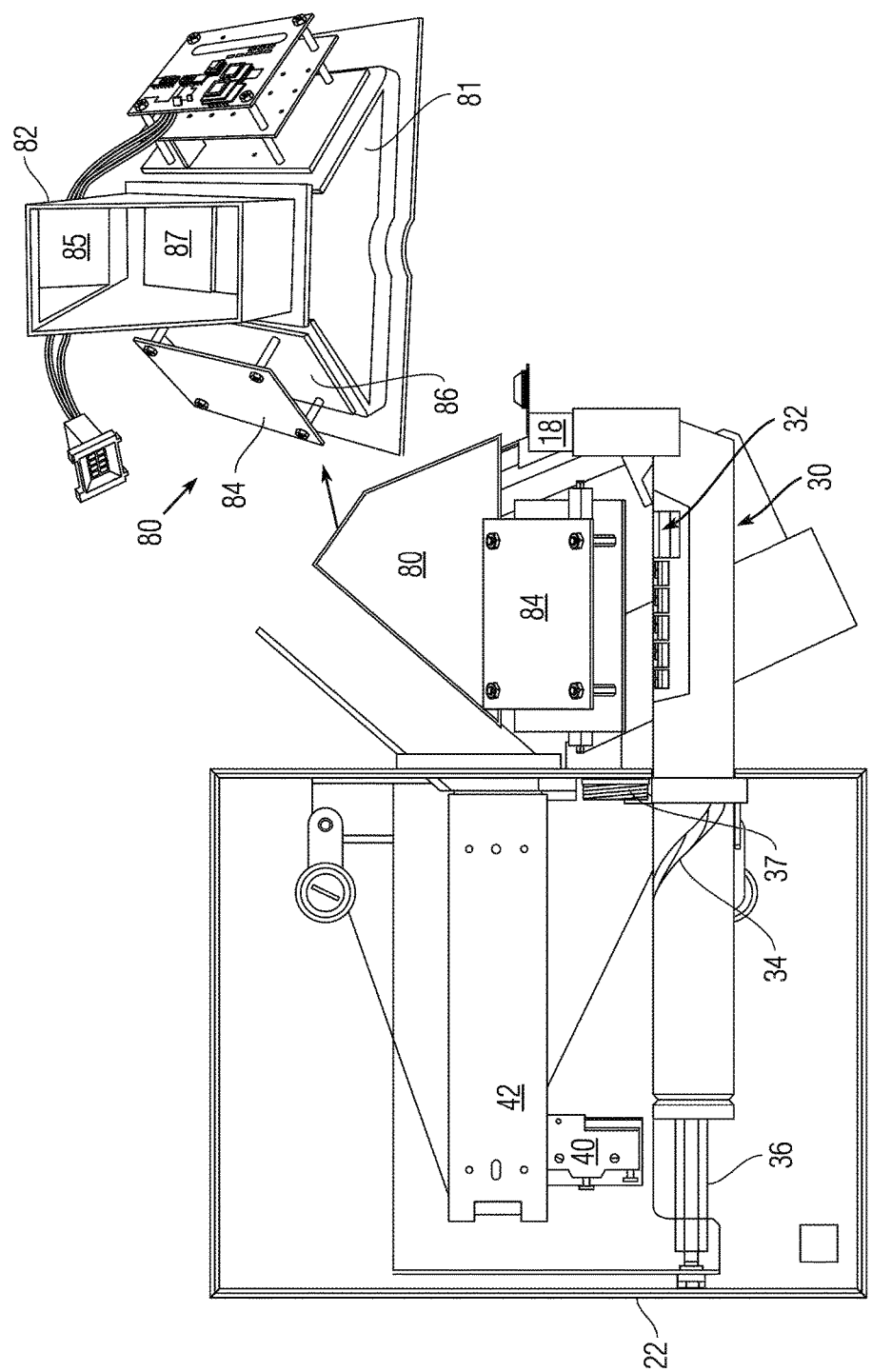
FIG. 8 is a side view of the kiosk 22 with housing removed and showing the details of the shuttle 30.

FIG. 8 is a side view of the kiosk 22 with front panel 23 removed and showing the details of the shuttle 30, as well as the lighting/magnification assembly 80.

The lighting/magnification assembly 80 (see inset) includes a chassis 81 that serves as a shroud to define an enclosed imaging station. The preferred chassis 81 includes two inclined diffuser sections 86 angled downward from the horizontal section. Two light panels 84 are laterally offset one on each side of chassis 81, each light panel 84 being mounted atop pylons slightly above a corresponding inclined diffuser 86 of chassis 81. Each light panel 84 comprises a plurality of LEDs mounted via raised pylons above the diffuser 86. In this instance a total of 64 LEDs are divided between the two offset printed circuit boards of light panels 84, each PC being held on either side of the sectioned chassis 81 at a 30 degree angle relative to horizontal for best lighting and minimum reflections/shadows. The LED lightpanels 84 are set back from the diffusers 86 to "smooth out" the lights, and minimize "hot spots". The two diffusers 86 are translucent white frosted panels and are fixed with screws, adhered or plastic welded to chassis 81 and used to spread light from the LEDs evenly inside the chassis 81. A shroud 82 is mounted atop chassis 81, and shroud 82 abuts the back of the tablet 24 to form an enclosure about its camera. The camera view is reflected \downward off an angled mirror 85 seated in shroud 82, through a sealed glass window 87 onto the imaging station 32 of shuttle 30. Chassis 81 and shroud 82 may be molded as a single piece.

Shuttle 30 generally comprises a cylindrical member having an imaging station 32 at the protruding end that is configured with a conforming recess for seating and positioning a test strip lengthwise. The recessed imaging station 32 is defined by a series of evenly-spaced partitions 39 extending radially the full cylindrical diameter of shuttle 30. The tips of partitions 39 are defined by a slot running coaxially with the shuttle 30 axis and defining a conforming recess for seating and centering a test strip. When seated therein, the partitions 39 separate each test pad on the test strip and create separate imaging backdrops therefor. The partitions 39 elevate the test strip preferably on sharp edges so as not to retain water. The recessed surface of shuttle 30 beneath the test strip is also rounded to improve water runoff. The ends of the conforming recess are also configured such that the test strip only rests on thin edges so that the surface tension of water on the test strip does not hinder the ejection of the test strip for the next test.

Figure 9:
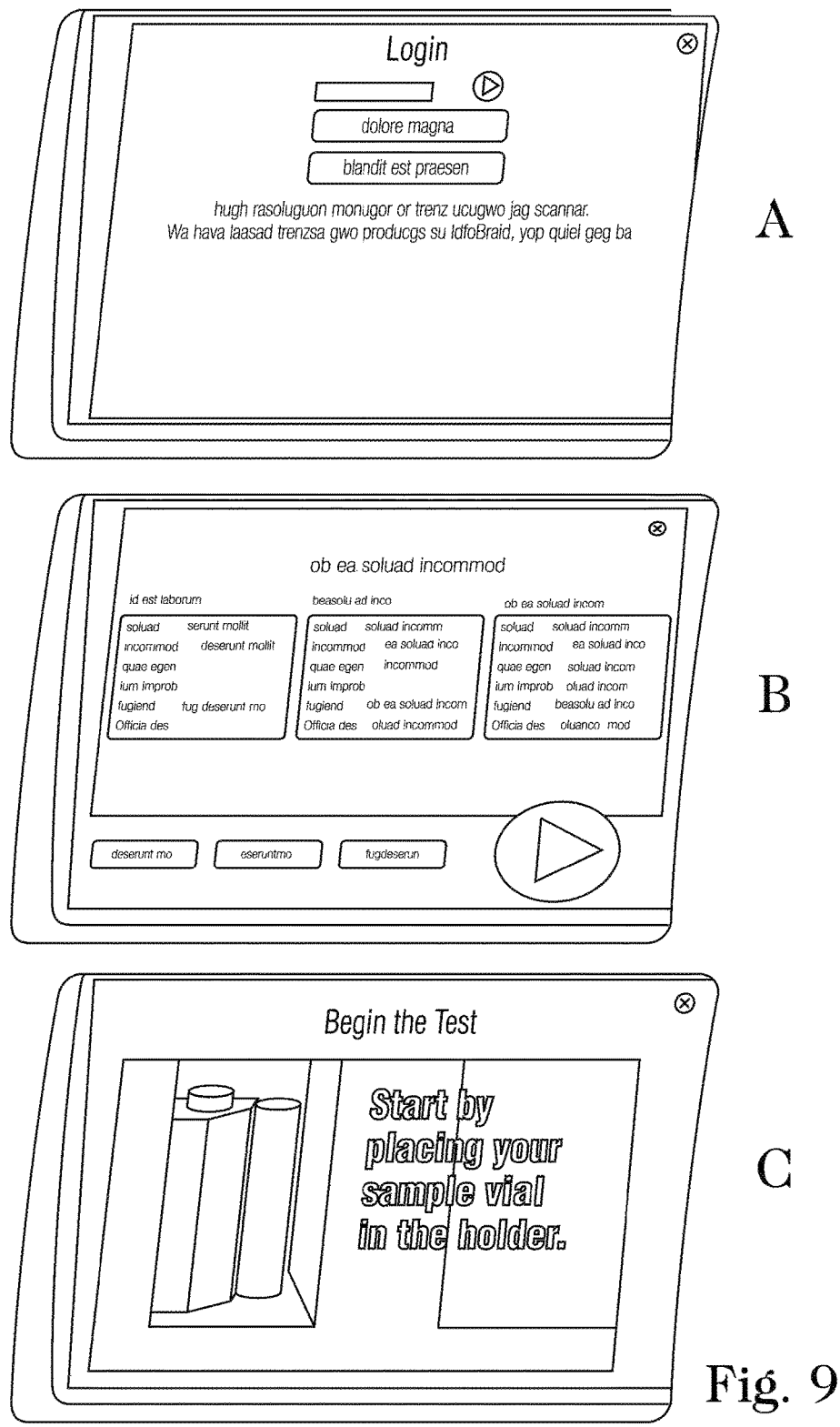
FIGS. 9A-G are a series of screen shots illustrating the software application user interface.
Figure 9:
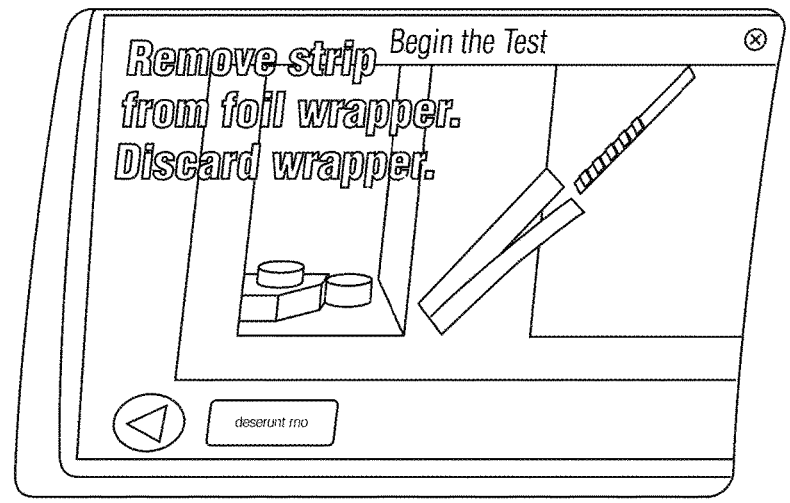
Figure 9:
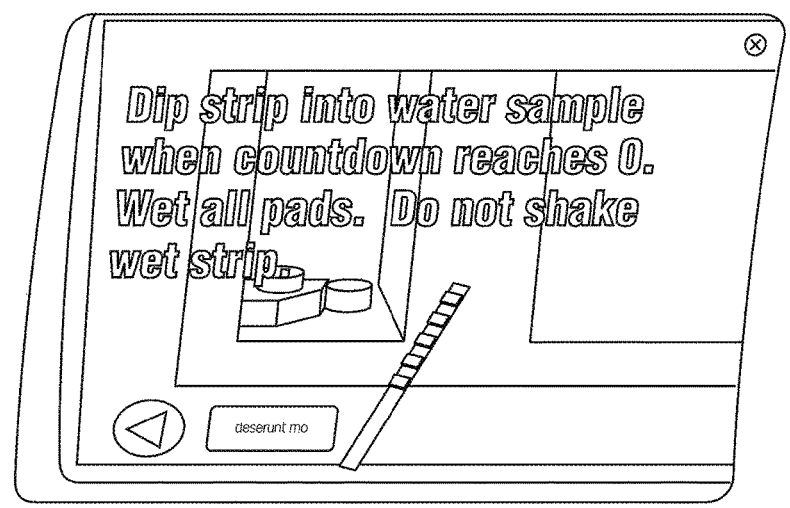
Figure 9:
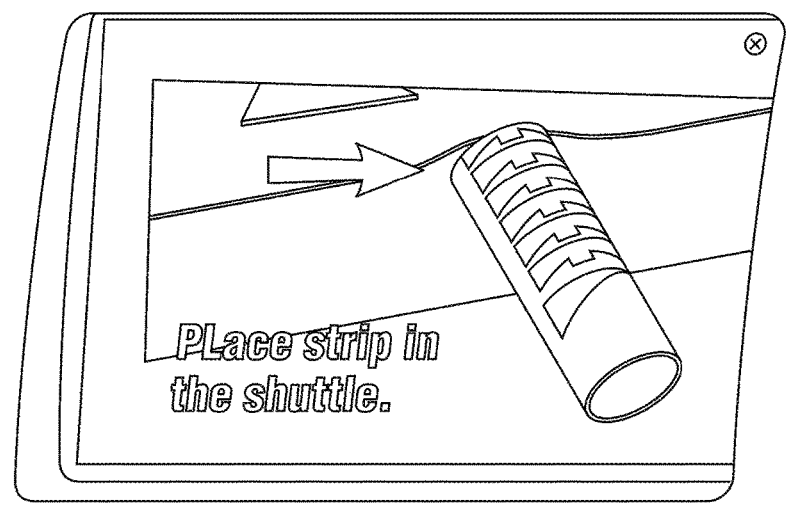

An electromechanical detent switch 40 mounted toward the rear of shuttle 30 extends a spring-arm 42 downwardly which, when encountered by shuttle 30 trips the switch to illuminate the two light panels 84 for imaging, when the shuttle 30 is fully inserted into the kiosk 22. Detent switch 40 may be equipped with a roller on its spring arm 42 that encounters the body of gas spring 36 then the shuttle 30 is in the imaging position. When the user presses the shuttle 30 to eject it, gas spring 36 biases the shuttle outward to provide a self-eject function. Shuttle 30 is slidably/rotatably mounted in housing 22 and is actively biased outward by gas spring 36, which is attached coaxially and internal to shuttle 30 and connected at the other end via bearing XX to trash bin 65. Thus, gas spring 36 is always pushing. The user overcomes the gas spring 36 to reinsert the shuttle 30 to the imaging position. The outer wall of shuttle 30 is defined by a curvilinear drive slot 34 which indexes rotation of shuttle 30 as it is being inserted (by the user) and/or ejected (by the cylinder 36). A guide pin 37 protrudes into slot 34 to index rotation, and the slot 34 is canted along the surface of the shuttle to force a pre-defined angle of rotation (approximately 120 degrees) during linear translation for the ejection of the strip. Guide pin 37 is a spring-loaded detent pin mounted on rolling type radial and thrust-bearings for lowfriction rotation, and it protrudes into slot 34 to guide its rotation. This rotation brings the test strip into full frontal exposure with the light panels 84 to the test strip whilst offsetting the camera 80 angle for imaging without reflectance. In order to ensure adequate rotation to eject the test strip reliably it has been found that the canted slot 34 requires a sharp elbow which is difficult for the cylinder to overcome when axially ejecting the shuttle 30. The low friction of the bearing arrangement in the spring-loaded bearing-mounted guide pin 37 compensates for this. When imaging is finished the shuttle 30 ejects and spins, dropping the used test strip into a refuse tray 65 below. Two additional design features are worthy of note. Referring back to FIG. 6 the distal end of shuttle 30 is equipped with a rotatable cap to prevent the consumer from applying any inadvertent torque and causing the shuttle 30 to skip the retracted position for imaging. Should the consumer twist the shuttle only the cap will spin. Also, it is possible to optionally mount a protruding pin 63 on the shuttle 30 as shown simply to knock down the pile of discarded test strips to make room for more. As seen in FIG. 9 touchscreen tablet 24 runs a software application that sequentially guides consumer stepby-step use with combined text and visual instructions. FIGS. 9A-G are a series of screen shots illustrating the software application user interface. As seen at FIG. 9A, the consumer initially logs into the system by telephone number, creates a new account, or elects to test without registering. As seen in FIG. 9B new/existing account information is presented to the user who may change/edit the information as needed. As seen in FIG. 9C, the system visually begins to walk the consumer through the testing process, beginning with placing the sample vial in the holder as shown. Next, as seen at FIG. 9D, the consumer is instructed to take a test strip from the kit and remove the foil wrapper. The foil wrapper is discarded in waste station 50 (FIG. 6). Next, at 9E, the consumer is instructed to dip the test strip into the sample vial after a predetermined countdown time (to ensure proper timing). At 9(F), the consumer is requested to press and ejects the shuttle 30, lays their test strip into the recessed imaging station 32, and reinserts the shuttle 30. Laying their test strip in the imaging station 32 in shuttle 30 seats the test strip at an indexed position and exposes each of the several test patches on the strip to the camera as the strip is facing upward.

Figure 10:
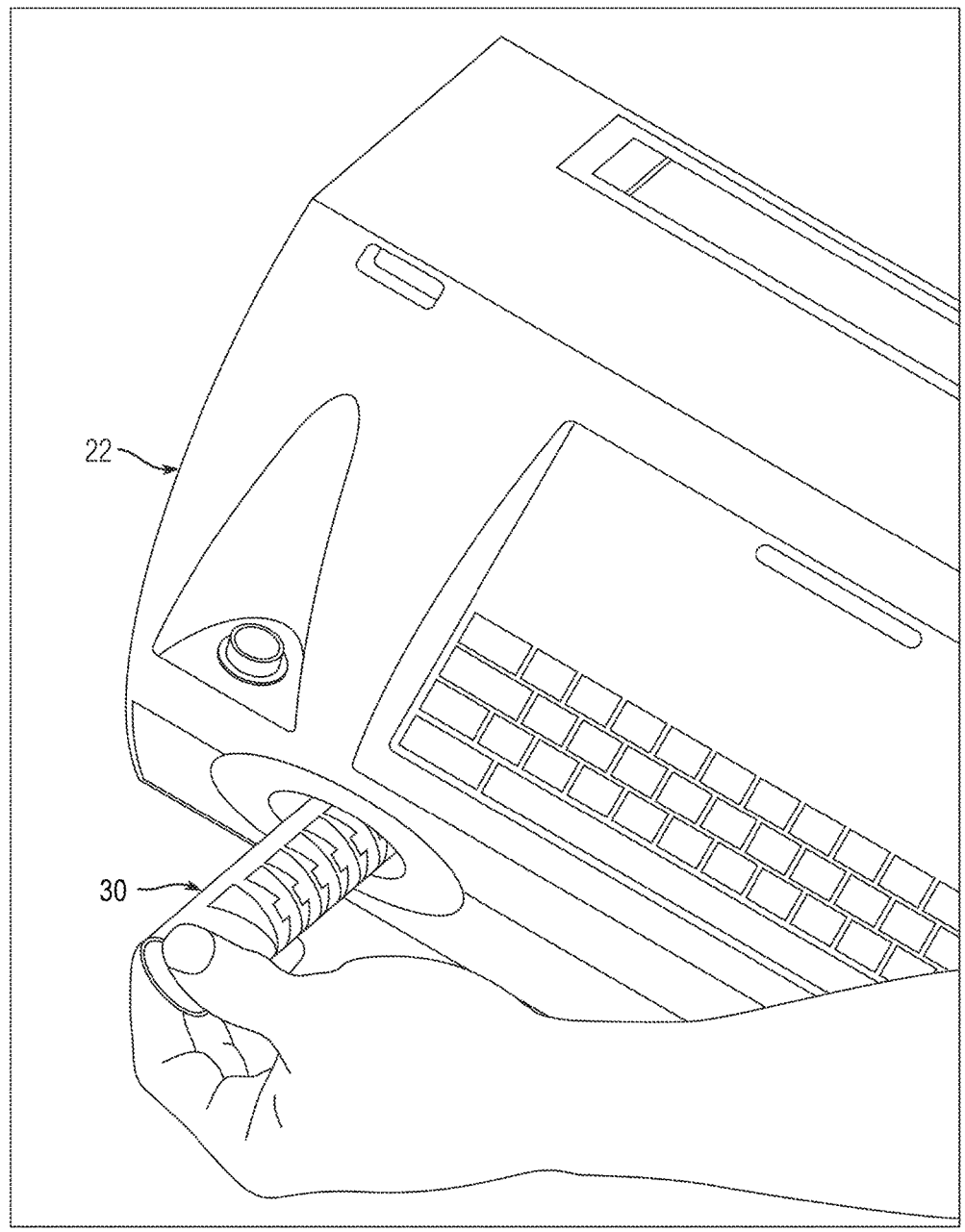
FIG. 10 illustrates a consumer reinserting the shuttle 30 into the kiosk.

FIG. 10 illustrates the consumer reinserting the shuttle 30 into the kiosk. As the shuttle 30 is manually inserted into the kiosk 22 the shuttle 30 eventually encounters the spring-arm 42 of switch 40 (FIG. 6), which illuminates light panel 84. The gas spring 36 continues retraction of shuttle 30 toward its imaging position, during which the guide pin 37 in drive slot 34 so that the test strip lies directly in from of the light panel 84 for full frontal illumination. In this imaging position the tablet 24 camera is directed through the lighting/ magnification assembly 80 at an angle (30 degrees) toward the test strip for imaging the strip without substantial glare interference to or from the illumination. Each window of shuttle 30 defined by partitions 39 lies situate beneath the lighting/magnification assembly 80 within the camera view, and the software application automatically triggers a still image frame from the tablet 24 camera. This image includes all test strip patches on the strip, and it is subjected to registration, calibration and colorimetric analysis as will be described. After complete imaging, the tablet 24 software application continues to guide consumer use with combined text and visual instructions, prompting them to eject the shuttle 30 once more. This rotates the shuttle 30 approximately 120 degrees causing the used test strip to fall out, and it falls into the lower refuse bin 65.

Referring to FIG. 9G, the tablet 24 software application sends the test results to cloud server and returns the results to the consumer. The main results comprise five critical factors that affect pool water chemistry, including free available chlorine (ppm), pH, total alkalinity (ppm), calcium hardness (ppm), and Cyanuric acid level (ppm). These five factors usually cause about 90% of all pool water problems. However, the ideal target at which to set them depends on subjective factors, and beneath the test results the user is prompted to enter these qualitative factors which include: 1) bather comfort; 2) visible algae; 3) water clarity; 4) water color: 5) surface stains; and 6) surface problems. The consumer is given the final option of pressing "Fetch Water Analysis Report" at bottom, in which case the combined quantitative results and qualitative results are transmitted to the cloud server for processing. This time, the cloud server returns treatment recommendations including recommended chemical levels and a store ticket for convenient in-store identification of the proper chemical products to purchase for attaining those levels.

Another imaging device according to the invention is a web-enabled computer 20 in communication with the cloud computing network 50 (FIG. 1). In this case end users access cloud-based applications 53 from a web-enabled computer 20. Cloud-based applications 53 may include, for example, the Taylorwise™ Water Analysis Software which is commercially available. The Taylorwise™ Water Analysis Software includes a treatment chemical product database with manufacturer recommended dosages for treatment chemicals in the database. The Taylorwise™ Water Analysis Software provides the ability to upload colorimetric test results, save them as test histories along with customer notes, and download treatment recommendations. The software can be used to analyze tests results from any existing testing equipment, including most portable test kits that contains the tests for water balance, namely pH, alkalinity, and hardness.

Still another imaging modality according to the invention is a digital strip reader (DSR), which is better suited for remote imaging.

Figure 11:
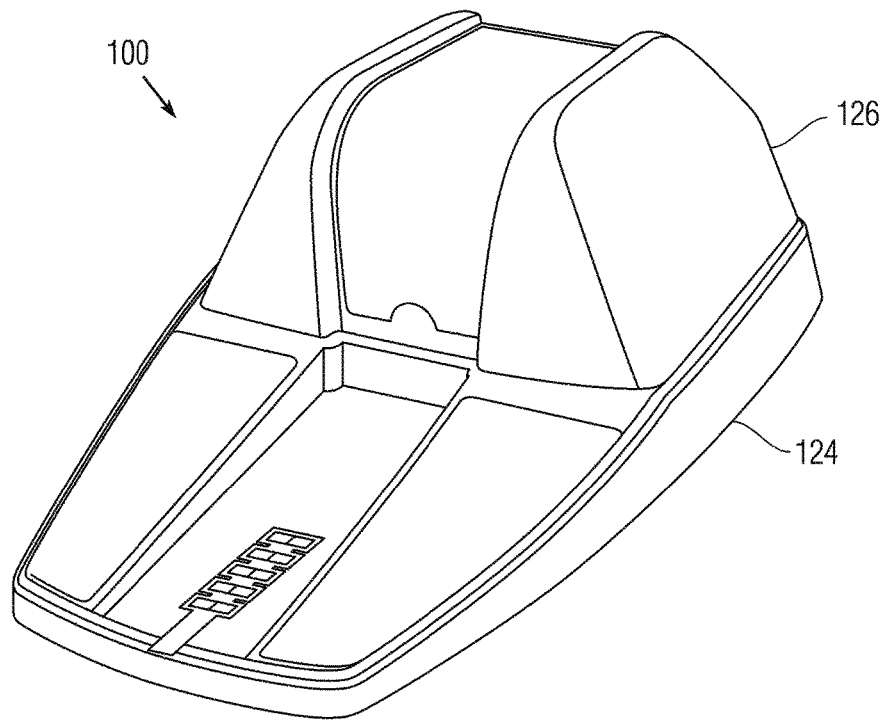
FIG. 11 illustrates an embodiment of the DSR 100 in accordance with the invention.

FIG. 11 illustrates an embodiment of the DSR 100 which generally includes a tabletop two-part housing comprising a bottom base 124 molded in a neutral gray for optimum imaging, and a plastic dome 126 partially covering base 124 and enclosing a camera 180 and controller circuit board.

Figure 12:
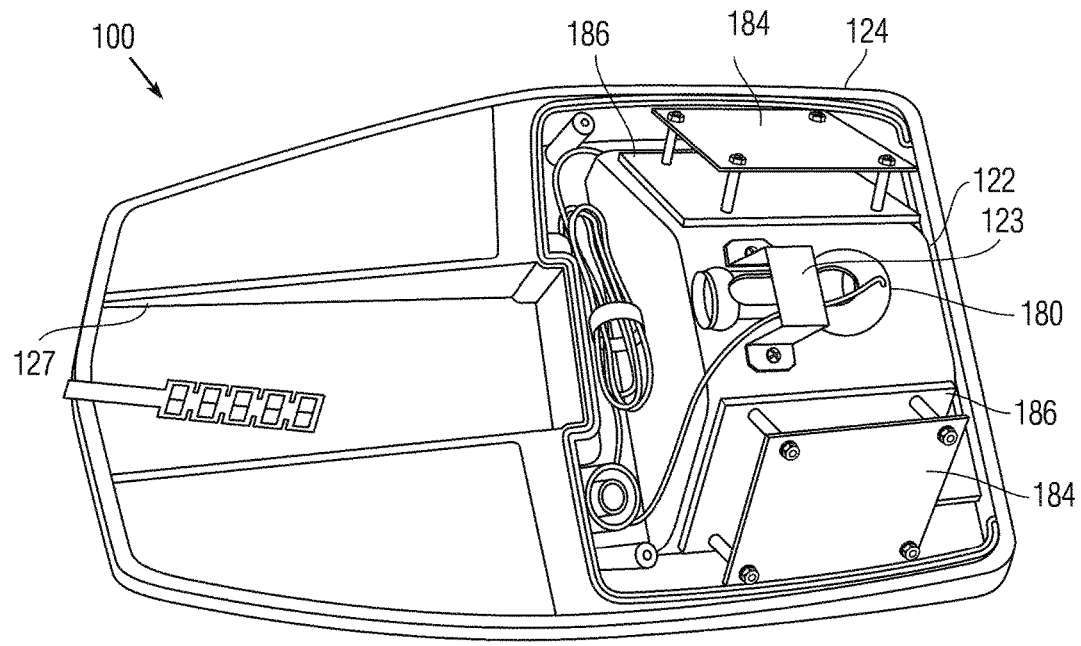
FIG. 12 shows outer shell 126 removed and exposing camera 180.

FIG. 12 shows outer shell 126 removed and exposing the camera 180, which in this embodiment comprises a VGA webcam such as a Logitech Pro 9000 webcam. An inner chassis 122 is mounted under the dome 126 and supports a camera 180. The chassis 122 serves as a shroud to define an enclosed imaging station. The preferred chassis 122 has a horizontal section, camera 180 being affixed to the horizontal section, plus two inclined diffuser sections 186 angled downward from the horizontal section. Two light panels 184 are laterally offset one on each side of camera 180, each light panel 184 being mounted atop pylons slightly above a corresponding inclined diffuser 186 of chassis 122. Each light panel 184 comprises a plurality of LEDs mounted via raised pylons above the diffuser 186. In this instance a total of 36 LEDs divided between the two offset printed circuit boards are used, each PC being held on either side of the sectioned shroud 122 at a 30 degree angle relative to horizontal for best lighting and minimum reflections/shadows. The LED light-panels 184 are set back from the diffusers 186 to "smooth out" the lights, and minimize "hot spots". The two diffusers 186 are translucent white frosted panels adhered or plastic welded to shroud 122 used to spreads light from LEDs evenly inside the chassis 122. Camera 180 is mounted on the horizontal section of chassis 122 via a screw-in bracket 123 and its aperture penetrates chassis 122 such that it images the interior imaging station.

The bottom piece 124 of the two-part housing defines a recessed track 127 that enters under chassis 122. A slidable plastic shuttle 130 is seated in the track. Shuttle 130 slides in and out from under the chassis 122 and dome 126. The shuttle 130 includes a tray to seat and position the test strip. The shuttle 130 allows the user to precisely position the test strip therein, and then move the test strip to the imaging station under chassis 122.

The camera 180 is connected to a controller board 182 (obscured beneath the shroud 122). The controller board 182 connects the unit to any remote PC computer via USB cable. The controller board 182 allows remote control of both the light panels 184 and camera 180, and also holds a battery and charging unit. The DSR 100 is powered only by the remote computer's USB connection, but the battery builds a reserve charge in-between uses to power LED light-panels 184.

As above the remote PC computer runs a local or cloud-based software application such as the Taylorwise™ Water Analysis Software, which for this purpose additionally includes a DSR control module. In operation, the DSR 100 is controlled entirely from the PC or cloud server 50 via this DSR control module. In sequence:

1) The user plugs in the DSR 100 and starts up the Taylorwise™ software;

2) The user either looks-up or adds a customer account. Once a customer is selected, the user can run a test (and assign it to that customer account).

3) To run a test, the user clicks on a "Run Test" button, which prompts the user to unwrap a test strip (also sold with the test kit to be described), discard the wrapping foil, and dip the test strip into vial 118.

4) After a predetermined time the user places the strip in the shuttle 130, and moves the strip by slide the shuttle 130 into the DSR 100 for the picture to be taken. All this is done according to a specific timing sequence, since timing is important to insure proper color development.

5) At the end of a predetermined countdown, the software sends a command to turn on the lights and take a picture of the test strip. This picture is displayed on the computer 20 screen. The software includes an automatic target recognition (ATR) module with the ability to recognize the imaged color patches or indexes located on the test strip and imaged with the camera 180. The ATR module "targets" the color patches on the test strip, but the user has the ability to adjust the areas of analysis by clicking and dragging GUI view boxes on the user interface. This allows correction if the ATR module targets the wrong area of the picture.

6) Once the user has viewed the picture, and confirmed the software is "targeting" the right area, he clicks "Get Results" and the colors are interpreted (based against a calibration table in the software). The calibrations are run with LAB color data and are adjusted back with reference to a master device as described below. The analyzed color values are applied to a lookup table to determine the test results on the test strip.

Still another image reader modality according to the invention is a smartphone 24 adapted for digital test-strip imaging and analysis. The smartphone 24 runs a software application for Apple® iPhone®, Android® or other devices which effectively turns the smartphone into a test strip scanner. The user dips a test strip, scans it using the camera on the phone, and gets treatment recommendations from cloud server 50 within seconds, all in real time.

Figure 13:
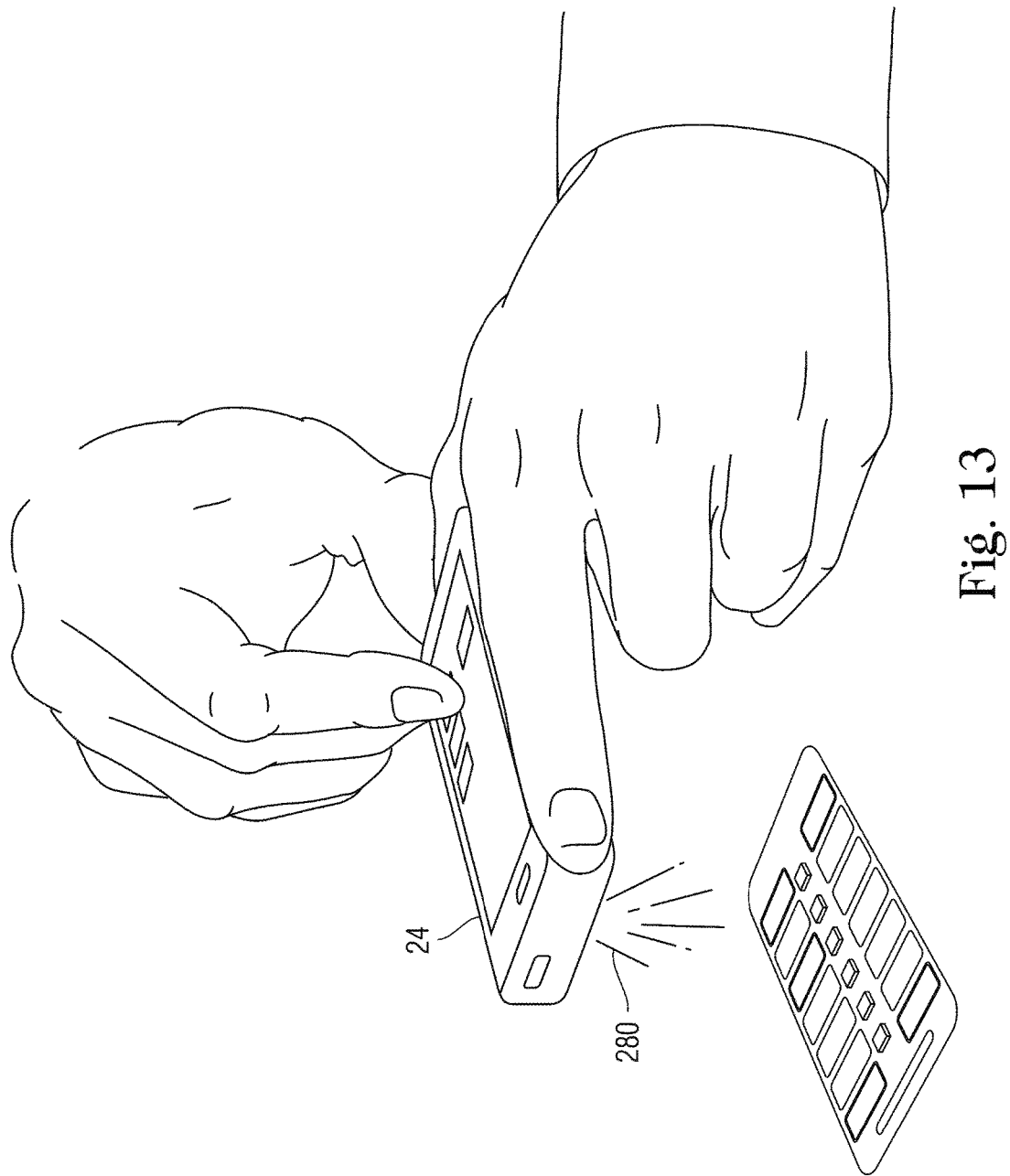
FIG. 13 illustrates an exemplary smartphone 24 in accordance with the invention.

FIG. 13 illustrates an exemplary smartphone 24 which is an Apple™ iPhone®, though any other smartphone with integrated camera will do. As above the smartphone 24 runs a software application that presents a graphical user-interface. The user unwraps a test strip (also sold with the test kit to be described), discards the wrapping foil, places the strip on any flat surface, and uses the software application to image the strip. The imaging and analysis process is completed automatically using the smartphone 24 onboard camera 280. In this instance, the imaging process is more complex than with dedicated imagers described above. In order for a smartphone 24 to take an image of an analytical test strip, it must intelligently locate the test pads and reference colors on the strip, average and eliminate variations in those colors, and adjust that the image based on the reference colors to account for variability.

In all the foregoing embodiments the imaging and analysis process bears similarity. However, because the smartphone 24 or on-board tablet of kiosk 22 camera have many sources of variability including differences in the image-capture-hardware (different smartphones/tablets each with different cameras will take different photos); variation within the same hardware, external variation such as ambient-lighting-environments, shadows, reflections, etc. Since lighting is uncontrolled for the smartphone 24, the image registration and calibration process is most stringent for the smartphone 24 and the process will herein be described with reference thereto.

Figure 14:
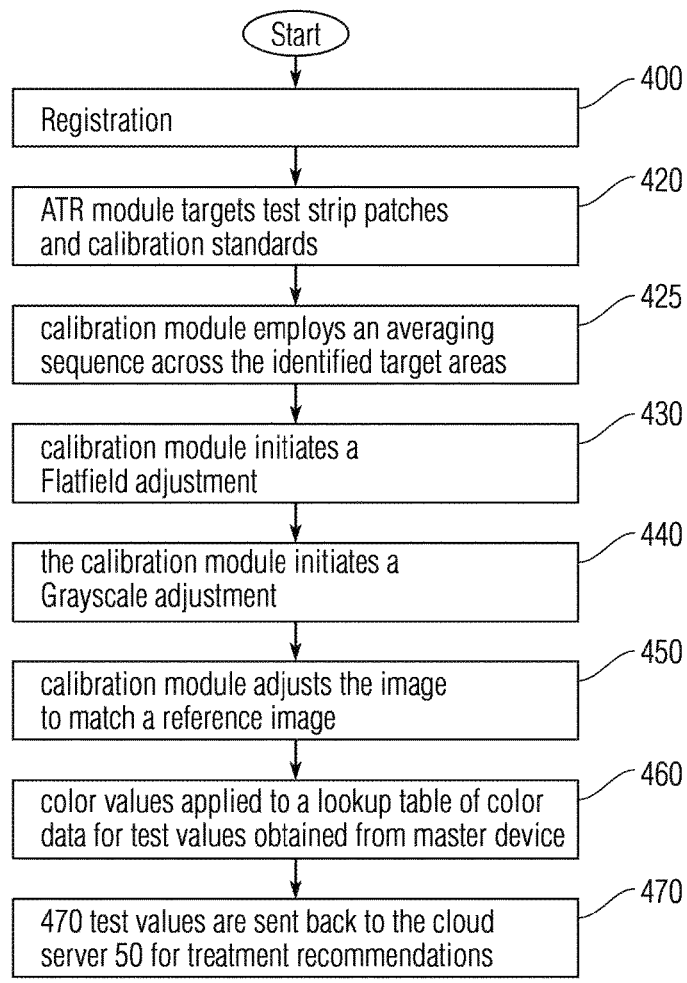
FIG. 14 is a block diagram of the entire imaging and analysis process.

FIG. 14 is a block diagram of the imaging and analysis process.

At step 400 the ATR module process begins with registration, e.g., locating the test strip in the captured image. Registration is important due to the wide variation of image quality across devices and lighting environments. Complicating factors include the relative distance of the camera from the target, orientation, focus, motion blur, and exposure. The present process achieves a high quality registration by use of a reference target to establish four known corner points, and then uses those points to locate the remaining box locations of interest. Referring back to FIG. 2, the process uses a reference "target" and the user is instructed to place the test strip on the target. The target includes four black circular registration marks 133 at the outside edge of the area of interest. The five-patch test strip is aligned and placed along the middle column B, and five "gray blocks" (A at left) and five "white blocks" (C at right) flank the area where the test strip is placed. With camera on, a live native resolution video feed is displayed on the display screen overtop a centering background, which presently comprises a large blue rectangle also displayed on the screen. The user is directed to center and position the image such that the four registration marks 133 fall just inside the four corners of the centering background. At the end of a predetermined count-down a video stream is recorded. In practice, users hands tend to shake and shift, and one skilled in the art will also understand that it is possible to monitor the video stream and get an automatic registration, refining continuously as the camera focuses and adjusts for exposure. Either way, a video stream is captured over a predetermined timeframe and the first captured still image displayed. If the registration did not yield "good enough" results, the user has the opportunity to manually relocate the registration points 133, allowing the remainder of the registration process to proceed on an image that was captured within a valid timeframe for the test. Given a recorded video stream the software performs an image analysis to locate the dead center of each of the four registration marks in each recorded frame of video. For each point 133 this image analysis looks for a black circle of some size against a white background, and takes into account that the marks 133 may not be in perfect focus or may be mis-oriented in such a way that they are not perfect circles in the image. The image analysis employs an extremely efficient two-step pattern recognition algorithm that first samples the video frame, traveling a spiral sampling pattern, sampling pixels at given locations beginning at a central (expected) location of the mark 133 and working its way outward along a spirical path. The sampling points are spaced to insure that the mark 133 cannot fall between samples.

Figure 15:
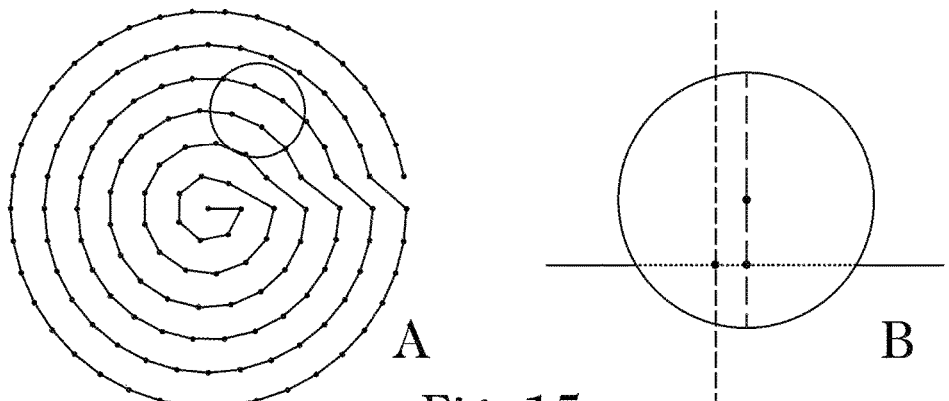
FIG. 15(A) illustrates the spiral search pattern used for image registration.
FIG. 15(B) illustrates the centering algorithm.

FIG. 15(A) illustrates the spiral search pattern with samples spaced at one third the size of the target mark 133. Pixel sampling proceeds along the spiral path looking for a dark region against a light region. Each pixel is converted to a single gray value by averaging the red, green, and blue RGB components. In the data stream, RGB pixel values fall between 0-255, but these are converted to a singular gray value within the canonical space 0-1. Although a "strict" definition of a dark pixel would be one with grayscale value of 0.2 or less, the present approach is probabilistic and creates a probability of acceptance as follows:

$$(gray < threshold) \text{ AND } (random(\ ) < sqrt(1.0(gray/threshold)))$$

A proper threshold has been experimentally determined to be 0.333.

Once the above-described sampling roughly establishes the location for the mark 133, a centering algorithm finds the mark 133 dead center. FIG. 15(B) illustrates the centering algorithm progressing from a rough center location for the mark 133 shown in blue. The centering algorithm notes the color of the pixels immediately surrounding the sample location, and walks horizontally in the frame buffer, examining pixels to find the left and right edges of the region we are trying to center on. It is assumed that the region is symmetrical and has an aspect ratio approaching 1, and so the center of this horizontal region is likely on a vertical (yellow) line that bisects the entire region. Using this second estimate, we again examine the pixels in the frame buffer, this time along a vertical red line at the new horizontal center location. Once the top and bottom boundaries are identified, the midpoint of the horizontal and vertical line segments is taken to be the true center (the red dot) of the region of interest.

Since the location process is performed on a live video stream, the previously found location of a reference mark 133 is used at the beginning of each new frame. Finding the reference mark 133 in the first frame may require a hundred or more samples, but once it is located subsequent frames can maintain the location (even for a user with shaky hands) with only one to five samples. If the mark moves too far from its expected location (near the corners of the guiding blue box) the location search resets to the expected location and begins again. This prevents the algorithm from locking on to artifacts of the target that are not the registration marks as the user finds the image. Again, in the last phase of registration, the first frame of the captured video stream is displayed to the user with the registration marks 133 identified.

At step 410 the ATR module provides a user interface to allow the user to adjust the areas of analysis by clicking and dragging GUI view boxes on the user interface. This allows correction if the ATR module has somehow targeted the wrong area of the picture. The user visually confirms that the marks 133 are accurately identified and located, and if not the user has an opportunity to manually identify the registration mark 133 locations using the user-interface (a finger-touch interface if on smartphone 22). For ease of selection the software automatically selects the most proximate mark to touch-contact. Once the user has viewed the picture, and confirmed the software is "targeting" the right area, he clicks proceed and the center points for the marks 133 are saved. Next, the box locations for each test strip and reference patch (columns A-C of FIG. 2) are calculated using their expected locations relative to the identified registration marks 133. The same spirical centering algorithm described above is used to identify the true center of each white/grey/colored sample box (Columns A-C of FIG. 2), and the color values for those boxes are determined using an averaging algorithm.

In addition, in an embodiment of the invention the expected range of values of the gray boxes (FIG. 2, column A) may be used to validate that the registration points 133 are indeed the correct points.

The algorithm then proceeds to analyze the sampled regions. Again, there are five gray reference boxes (col. A), five test strip patch boxes (B), and five white boxes that are sampled from the captured image. The white boxes (C) are used in an (optional) flat field calibration step. The gray boxes (A) are used to compute color corrections. Finally, the test strip boxes (B) are used to read the test strip that the user has dipped in their pool water and placed on the target.

At step 425 a calibration module employs an averaging sequence across the identified target areas to account for variation/glare/abnormalities in test strip and calibration color standards. The video imaging process is inherently prone to pixel variance across each sample region. This is evident when watching any video feed of a stationary object, where pixels flicker. The pixel variance is typically on the order of 1%-5%, and so the averaging process eliminates variance. For each sample box a small area in the center region of the sample box location is examined. The mean and standard deviation are computed, and then the entire sample box is examined pixel-by-pixel. Only pixels within 2 standard deviations of the mean pixel are accepted, and a new mean value is calculated. This mean is used as the sample value for that box.

Once the mean sample values are extracted for each sample box in the image, a series of calibrations are made to derive accurate test value readings.

At step 430 the calibration module initiates a Flatfield adjustment to account for lighting variations (shadows) within a given picture. Flatfield adjustments for all sample regions are calculated from white-only sample regions (FIG. 2(C), and applied to all other sample regions. The flatfield adjustment assumes that these areas should be "white", and compensates for any variation. For the kiosk 22, a simple linear adjustment of the sampled values is sufficient. In other cases, more complex corrections may be necessary. An example flatfield calculation for the kiosk is shown in the sample calculation walkthrough, below.

At step 440 the calibration module initiates a Grayscale adjustment to account for variation in image-capture-hardware (RGB/gamma distribution/etc.), device-specific-graphic-interpretations (different OS, drivers, graphics cards, etc.), and ambient lighting environment (indoor/outdoor/etc.). The present approach avoids adjustment to any fixed calibration standard, but instead uses a "master image" captured from a master reference device. Color corrections for the entire image are computed using known color calibration chip values from a Master device and the measured values of color calibration chip sample regions (FIG. 2, col. C) on the Client imaged target. These corrections are applied to the sample regions corresponding to the water tests on the test strip. The Master device is configured in a stationary location with a consistent full spectrum lighting environment similar to daylight. A target and test strip dipped in water with known characteristics is imaged on the Master device and the position of the image adjusted so that components of the target are in known locations in the image, and the same the ATR module process is performed to yield Master Color Tables as follows:

Master Color Tables

| Gray | | |
|---|---|---|
| R | G | B |
| 2 | 2 | 2 |
| 1 | 1 | 1 |
| 1 | 1 | 1 |
| 9 | 8 | 8 |
| 4 | 4 | 5 |

| Free Chlorine | | | |
|---|---|---|---|
| Standard | R | G | B |
| 0 | 2 | 2 | 1 |
| 0.5 | 2 | 1 | 1 |
| 1 | 1 | 1 | 1 |
| 1.5 | 1 | 1 | 1 |
| 2 | 1 | 1 | 1 |
| 2.5 | 1 | 1 | 1 |
| 3 | 1 | 1 | 1 |
| 4 | 1 | 1 | 1 |
| 5 | 1 | 1 | 1 |
| 7.5 | 1 | 9 | 1 |
| 10 | 1 | 8 | 1 |

| pH | | | |
|---|---|---|---|
| Standard | R | G | B |
| 6.40 | 2 | 1 | 1 |
| 6.60 | 2 | 1 | 1 |
| 6.80 | 2 | 1 | 1 |
| 7.00 | 2 | 1 | 1 |
| 7.20 | 2 | 1 | 1 |
| 7.35 | 2 | 1 | 1 |
| 7.50 | 2 | 1 | 1 |

-continued pH

| Standard | R | G | B |
|---|---|---|---|
| 7.65 | 2 | 1 | 1 |
| 7.80 | 2 | 1 | 1 |
| 8.10 | 2 | 1 | 1 |
| 8.40 | 2 | 9 | 1 |

Total Alkalinity

| Standard | R | G | B |
|---|---|---|---|
| 0 | 2 | 1 | 1 |
| 20 | 1 | 1 | 1 |
| 40 | 1 | 1 | 1 |
| 60 | 1 | 1 | 1 |
| 80 | 1 | 1 | 1 |
| 100 | 1 | 1 | 1 |
| 120 | 1 | 1 | 1 |
| 150 | 1 | 1 | 1 |
| 180 | 9 | 1 | 1 |
| 210 | 8 | 1 | 1 |
| 240 | 8 | 1 | 1 |

Total Hardness

| Standard | R | G | B |
|---|---|---|---|
| 0 | 8 | 1 | 1 |
| 50 | 1 | 9 | 1 |
| 100 | 1 | 9 | 1 |
| 150 | 1 | 8 | 1 |
| 200 | 1 | 8 | 1 |
| 300 | 1 | 8 | 1 |
| 400 | 1 | 8 | 1 |
| 600 | 1 | 8 | 1 |
| 800 | 1 | 7 | 1 |

Cyanuric Acid

| Standard | R | G | B |
|---|---|---|---|
| 0 | 2 | 1 | 7 |
| 30 | 2 | 1 | 7 |
| 60 | 2 | 1 | 7 |
| 80 | 2 | 1 | 8 |
| 100 | 2 | 1 | 9 |
| 150 | 2 | 1 | 1 |
| 200 | 1 | 9 | 1 |
| 250 | 1 | 8 | 1 |
| 300 | 1 | 6 | 1 |

The Master Tables are created by a process of repeated readings on the Master device. Each water characteristic is measured using a sample with known qualities, and the experiment repeated a sufficient number of times to yield high confidence and low variance in that reading Given the Master Tables, and referring back to FIG. 14, at step 450 the calibration module adjusts the sample image back to match the Master Tables taken on the master device. Color corrections for the entire image are computed using the known color calibration chip values from the Master device, and the measured values of color calibration chip sample regions on the client-imaged target (FIG. 2, col. C). These corrections are applied to the sample regions corresponding to the water tests on the test strip (FIG. 2, col. B).

The foregoing steps 410-450 are repeated across the range of water qualities that the test strips can be used to measure, and the full range of tests are repeated until the average values of each individual water quality test and calibration chip have sufficiently low variance (this eliminates testing variations as a source of error for the master values and gives an indication of the expected accuracy of client testing). The sample regions of the image corresponding to the water tests on the test strip are examined and the color values recorded.

At step 460 the color values are applied to a lookup table of color data for test values, also obtained from the Master Device. The final color selections for each test pad (FIG. 2, col. B) are analyzed for analyte ppm by reference to a lookup table. For the above-referenced DSR this analysis entails a RGB to LAB color data conversion, as calibrations and comparisons are run with LAB color data. Otherwise, for iPhone® 24, web-enabled computer 20, dedicated in store kiosks 22, RGB is used. This analysis entails a RGB to LAB color data conversion, as calibrations and comparisons are run with LAB color data. The sampled color values are compared against the tabular results of water characteristics compiled using the Master to compute a ""distance"" to each color value. The two closest values for each test are interpolated to get the water characteristics.

At step 470 tested values are sent back to the cloud for treatment recommendations. The software correlates the test results to analysis and treatment recommendations, which are returned and displayed in real time.

Referring back to steps 430-460, the cameras 80, 180 or typical smartphone 24 cameras will capture an image and represent color using 16 or 24-bit RGB values. However, due to the above noted differences in image capture using the DSR, RGB values are not regarded as standard values. Instead, there are fixed standards such as CIE tristimulus values X, Y, Z, or the so-called CIELAB values (L*, a*, b*). For the DSR the present system employs a two-part normalization of the RGB data, followed by a RGB to LAB color data conversion, and comparisons with reference LAB color data. The two-part normalization of the RGB data entails 1) flatfield adjust RGB values (step 430); and/or 2) Grayscale adjustment of the RGB values (step 440). The results are used to adjust the image back to the way that the image would have appeared on a reference camera/computer (step 450), so that a more accurate analysis can be performed on the standardized image. The method is reduced to practice for analysis of a test strip, used in the analysis of water, for the pool and spa market, and for use with a smartphone and/or webcam.

Step 430: Flatfield Adjust (Optional)

Flat fielding is a fairly well-known calibration technique that requires the acquisition of two calibration frames. First, a bias frame or a dark frame is taken which clears the camera 80, 180 of any accumulated charge, and the dark image is read out the cleared camera CCD. The resulting image is a low signal value image in which all of the pixels have approximately the same value representing the electronic offset of the system. A second calibration image, a "flat field" frame, is taken. This is a white frame at full illumination designed to measure the response of each pixel in the CCD array to correct for any variation in illumination over the field of the array. In the present case, both flatfield images are taken of reference white and dark patches resident on each test pattern strip.

Step 440: Grayscale Adjust

The grayscale adjust uses the image of a grayscale master strip with six gradiated gray patches M1-M6 as a reference. This grayscale master image is taken at step 400 by a master reference device configured in a stationary location with consistent lighting and is stored at cloud computing services 53. The grayscale adjust also employs a greyscale calibration strip with gradiated gray patches C1-C6 imaged at a test strip reader device 20, 22, 24, 26. The test strip reader device 20, 22, 24, 26 takes a RGB color frame of the greyscale calibration strip and grayscale master image is then used to arrive at a grayscale adjustment value for the actual image S of each test strip patch (FIG. 2 col. B). More specifically, the image of the grayscale calibration strip bears gradiated gray patches C1-C6, resulting in test colors T1-T6 each having RGB values. The present method generally takes the sample test strip value (S) and multiplies it by a correction factor (M/T) to map it back to value that it would have read on the master cloud services 53. More specifically, it grayscale-adjusts each color value (R, G, and B) for each test color T1-T6 with a correction factor (Mn/Cn) to adjust it toward the six gradiated gray patches M1-M6 on the reference master. Importantly, since the calibration strip test colors T1-T6 might fall between patches C1-C6 (e.g., the strip value (S) might fall between two standard points T2 and T3), the present method interpolates the difference when applying the correction factor. Specifically, each actual sample test color S is corrected based on an interpolation of the difference between the gray patches M1-M6 on the reference master and the difference between the gray patches C1-C6 on the calibration strip and the correction factor applied as follows:

Grayscale Adjusted $S$ value=$(S-C3)/(C2-C3)*(M2-M3)+M3$.

Figure 16:
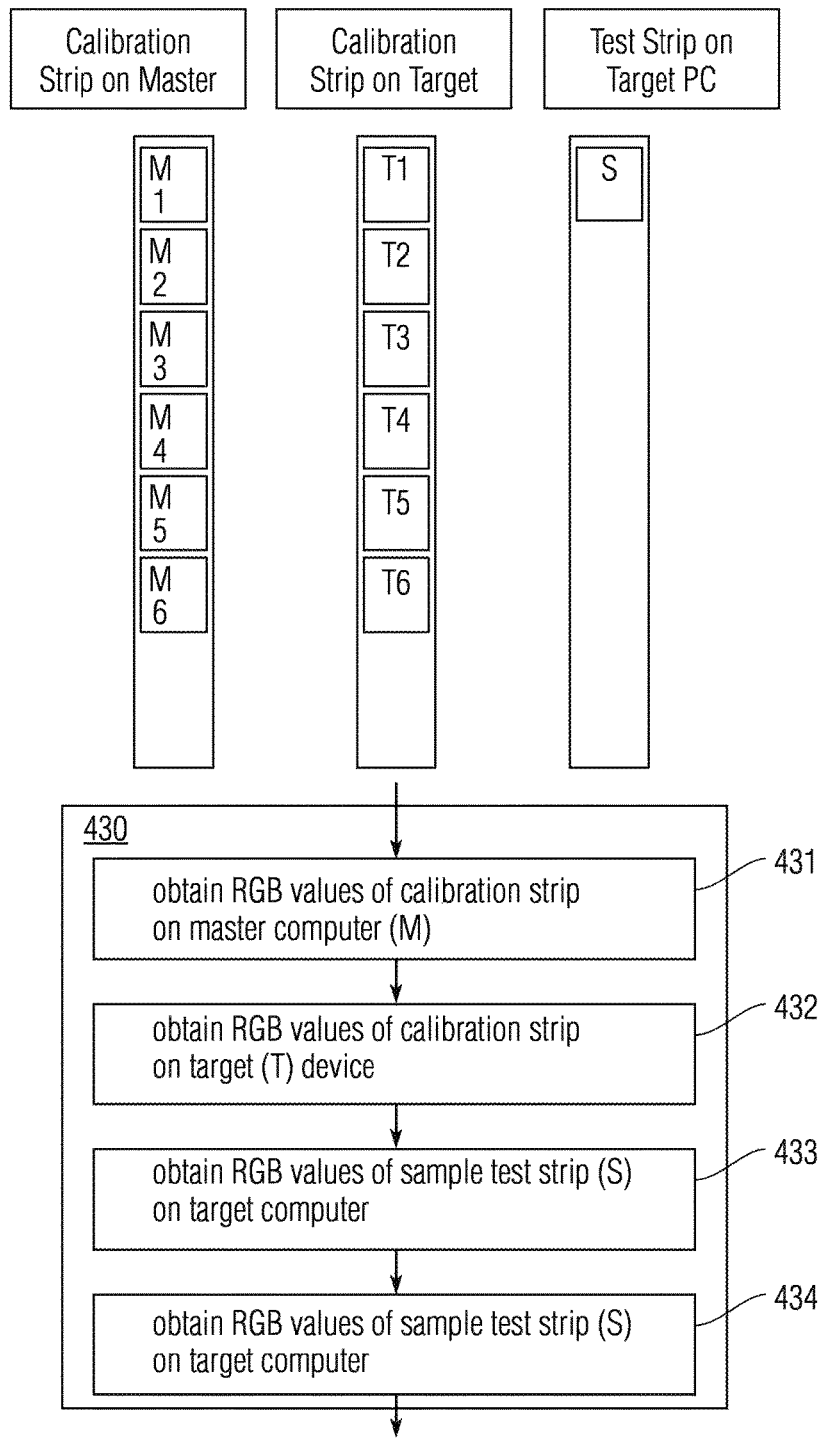
FIG. 16 is a more detailed diagram of the substep s of step 430 of FIG. 14.

FIG. 16 is a block diagram illustrating the foregoing substeps of step 430, which are broken down as follows:

Step 431: obtain RGB values of calibration strip on master computer (M);

Step 432—obtain RGB values of calibration strip on target (T) (test strip reader device 20, 22, 24, 26);

Step 433—obtain RGB value of sample test strip (S) on target computer (test strip reader device 20, 22, 24, 26);

Step 434—Grayscale adjust each sample value (S) by applying a correction factor that adjusts the image RGB value of sample test strip (S) back to how that image would have read had it been taken on the master computer. The Grayscale Adjusted S value=$(S-T3)/(T2-T3)*(M2-M3)+M3$.

The different grayscale colors break up the color space into areas and allow this calculation of a different correction factor for each specific point in the color space.

The following is an example of the calculations employed at steps 430-470 showing registration, color correction, and value matching to yield test results, using the Master Reference Tables shown above.

| grayBoxColors |
|---|
| 0 (0.858, 0.836, 0.730) |
| 1 (0.637, 0.617, 0.544) |
| 2 (0.584, 0.564, 0.496) |
| 3 (0.407, 0.390, 0.351) |
| 4 (0.142, 0.136, 0.137) |

| whiteBoxColors |
|---|
| 6 (0.974, 0.967, 0.896) |
| 7 (0.999, 0.998, 0.929) |

| whiteBoxColors |
|---|
| 8 (1.000, 1.000, 0.954) |
| 9 (0.999, 0.999, 0.916) |
| 10 (0.992, 0.987, 0.905) |
| 11 (0.938, 0.927, 0.846) |

| padBoxColors |
|---|
| 0 (0.893, 0.886, 0.786) |
| 1 (0.849, 0.519, 0.468) |
| 2 (0.542, 0.642, 0.398) |
| 3 (0.525, 0.315, 0.469) |
| 4 (0.780, 0.523, 0.207) |

| flatFieldAdjustmentVectors |
|---|
| 0 (1.027, 1.034, 1.064) |
| 1 (1.001, 1.002, 1.027) |
| 2 (1.000, 1.000, 1.000) |
| 3 (1.001, 1.001, 1.042) |
| 4 (1.008, 1.013, 1.054) |
| 5 (1.066, 1.079, 1.128) |

| flatFieldAdjustedGrayBoxColors |
|---|
| 0 (0.870, 0.851, 0.763) |
| 1 (0.638, 0.617, 0.552) |
| 2 (0.584, 0.564, 0.506) |
| 3 (0.409, 0.393, 0.368) |
| 4 (0.147, 0.142, 0.149) |

| flatFieldAdjustedPadBoxColors |
|---|
| 0 (0.905, 0.902, 0.822) |
| 1 (0.849, 0.520, 0.475) |
| 2 (0.543, 0.643, 0.406) |
| 3 (0.527, 0.317, 0.491) |
| 4 (0.809, 0.546, 0.225) |

| colorCorrectionVectors |
|---|
| 0 (1.000, 1.000, 1.000) |
| 1 (1.037, 1.028, 1.120) |
| 2 (1.021, 1.017, 1.138) |
| 3 (0.873, 0.869, 0.954) |
| 4 (0.893, 0.839, 0.885) |
| 5 (1.305, 1.269, 1.313) |
| 6 (1.000, 1.000, 1.000) |

| colorCorrectedPadBoxColors |
|---|
| 0 (0.930, 0.919, 0.896) Free Chlorine |
| 1 (0.880, 0.448, 0.445) - pH |
| 2 (0.476, 0.654, 0.367) - Total Alkalinity |
| 3 (0.464, 0.307, 0.465) - Total Hardness |
| 4 (0.835, 0.473, 0.262) - Cyanuric Acid |

| masterGrayColorVectors |
|---|
| 0.000 -> (1.000, 1.000, 1.000) |
| 0.000 -> (0.902, 0.875, 0.855) |
| 0.000 -> (0.651, 0.627, 0.627) |
| 0.000 -> (0.510, 0.490, 0.482) |
| 0.000 -> (0.365, 0.329, 0.325) |
| 0.000 -> (0.192, 0.180, 0.196) |
| 0.000 -> (0.000, 0.000, 0.000) |

| freeChlorineColorVectors |
|---|
| 0.000 -> (0.843, 0.824, 0.780) |
| 0.500 -> (0.808, 0.749, 0.757) |
| 1.000 -> (0.776, 0.675, 0.733) |
| 1.500 -> (0.757, 0.616, 0.722) |
| 2.000 -> (0.733, 0.553, 0.706) |
| 2.500 -> (0.710, 0.506, 0.682) |
| 3.000 -> (0.686, 0.455, 0.655) |
| 4.000 -> (0.663, 0.431, 0.631) |
| 5.000 -> (0.635, 0.408, 0.604) |
| 7.500 -> (0.580, 0.369, 0.553) |
| 10.000 -> (0.525, 0.329, 0.502) |
| free Chlorine: 0.000 |

| phColorVectors |
|---|
| 6.400 -> (0.863, 0.733, 0.404) |
| 6.600 -> (0.863, 0.702, 0.416) |
| 6.800 -> (0.867, 0.671, 0.431) |
| 7.000 -> (0.863, 0.631, 0.443) |
| 7.200 -> (0.859, 0.592, 0.459) |
| 7.350 -> (0.855, 0.557, 0.459) |
| 7.500 -> (0.851, 0.522, 0.463) |
| 7.650 -> (0.847, 0.494, 0.475) |
| 7.800 -> (0.847, 0.467, 0.486) |
| 8.100 -> (0.839, 0.420, 0.510) |
| 8.400 -> (0.835, 0.376, 0.529) |
| pH: 7.800 |

| alkalinityColorVectors |
|---|
| 0.000 -> (0.804, 0.776, 0.404) |
| 20.000 -> (0.737, 0.741, 0.420) |
| 40.000 -> (0.667, 0.706, 0.435) |
| 60.000 -> (0.600, 0.675, 0.463) |
| 80.000 -> (0.537, 0.643, 0.494) |
| 100.000 -> (0.490, 0.616, 0.522) |
| 120.000 -> (0.447, 0.588, 0.549) |
| 150.000 -> (0.404, 0.569, 0.576) |
| 180.000 -> (0.365, 0.549, 0.608) |
| 210.000 -> (0.345, 0.537, 0.624) |
| 240.000 -> (0.322, 0.522, 0.643) |
| alkalinity 80.000 |

| totalHardnessColorVectors |
|---|
| 0.000 -> (0.329, 0.416, 0.612) |
| 50.000 -> (0.420, 0.388, 0.596) |
| 100.000 -> (0.514, 0.365, 0.576) |
| 150.000 -> (0.565, 0.345, 0.569) |
| 200.000 -> (0.616, 0.325, 0.557) |
| 300.000 -> (0.639, 0.322, 0.553) |
| 400.000 -> (0.663, 0.314, 0.553) |
| 600.000 -> (0.675, 0.314, 0.549) |
| 800.000 -> (0.690, 0.310, 0.549) |
| total Hardness: 100.000 |

| cyanuricAcidColorVectors |
|---|
| 0.000 -> (0.843, 0.631, 0.282) |
| 30.000 -> (0.839, 0.604, 0.294) |
| 60.000 -> (0.831, 0.576, 0.302) |
| 80.000 -> (0.824, 0.545, 0.333) |
| 100.000 -> (0.820, 0.518, 0.361) |
| 150.000 -> (0.796, 0.447, 0.392) |
| 200.000 -> (0.773, 0.376, 0.420) |
| 250.000 -> (0.753, 0.318, 0.435) |
| 300.000 -> (0.729, 0.294, 0.447) |
| cyanuric Acid: 80.000 |

It should now be apparent that the above-described system and method provides a cross-platform web-based solution for water testing capable of measuring, analyzing and maintaining the quality of water using a plurality of different test strip readers, all calibrated by a combination of local and cloud-based software for more consistent results.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

The invention claimed is:

1. A cloud-based system for water testing, comprising:
a cloud computing network including at least one web-enabled computer having a processor, a computer readable non-transitory storage medium, and software comprising instructions stored on said non-transitory storage medium for receiving a set of colorimetric values corresponding to a test sample, calculating analyte parts-per-million (ppm) from said set of colorimetric values, and outputting said calculated analyte ppm;
a plurality of different test strip readers chosen from among a group comprising smartphones, kiosk computers, portable digital strip readers, and remote computers, all in communication with said cloud computing network, said plurality of different test strip readers all including a processor, a computer readable non-transitory storage medium, an on-board camera, and software comprising instructions stored on said non-transitory storage medium for providing a user interface to obtain a digital image of a reagent test strip by guiding alignment of said camera relative to a reagent test strip, for normalizing and analyzing color information in the digital image by colorimetric analysis, and for transmitting a set of colorimetric values corresponding to said digital image to said cloud-based computer system for analysis.

2. The cloud-based system for water testing according to claim 1, wherein said test strip reader software comprises instructions stored on said non-transitory storage medium to color-calibrate said camera.

3. The cloud-based system for water testing according to claim 1, wherein said test strip reader software comprises instructions stored on said non-transitory storage medium to facilitate taking said digital image by automatically targeting sample areas to image on a sample test strip, and by allowing a user to manually adjust the sample areas via said user interface.

4. The cloud-based system for water testing according to claim 3, wherein said test strip reader software comprises instructions stored on said non-transitory storage medium for automatically capturing multiple digital images across the identified targeted sample areas and for averaging, said multiple images to account for variation.

5. The cloud-based system for water testing, according to claim 4, wherein said test strip reader software comprises instructions stored on said non-transitory storage medium for executing a flatfield adjustment of the averaged images to normalize lighting variations.

6. The cloud-based system for water testing according to claim 4, wherein said test strip reader software comprises instructions stored on said non-transitory storage medium for executing a grayscale adjustment of the averaged images relative to a reference image to normalize differences in said camera hardware.

7. The cloud-based system for water testing according to claim 4, wherein said test strip reader software comprises instructions stored on said non-transitory storage medium for executing RGB to LAB color data conversion.

8. The cloud-based, system for water testing according to claim 1, wherein said a cloud computing network software comprises instructions stored on said non-transitory storage medium for receiving said set of colorimetric values corresponding to a test sample, and for calculating analyte parts-per-million (ppm) from said set of colorimetric values by reference to a lookup table.

9. A method for water testing, comprising the steps of providing software executable on a plurality of different test strip read ers chosen from among a group comprising smartphones, kiosk computers, portable digital strip readers, and remote computers, all of said test strip readers including a computer processor and computer readable non-transitory storage medium;

executing said software on one of said plurality of different test strip readers to instantiate a user interface; guiding a user by said user interface to capture a digital image of a reagent test strip; said executed software automatically normalizing and analyzing color information in the captured digital image by colorimetric analysis to produce a set of colorimetric values corresponding to said digital image;

transmitting said a set of colorimetric values to a remote computer system for analysis;

receiving said transmitted colorimetric values at said remote computer system; calculating at said remote computer system analyte parts-per-million (ppm) from said received set of colorimetric values; outputting said calculated analyte ppm back to said one of said plurality of different test strip readers; displaying said calculated analyte ppm to said user at said one of said plurality of different test strip readers.

10. The method for water testing according to claim 9, further comprising a step of automatically targeting sample areas to image on a sample test strip and allowing a user to adjust the sample areas.

11. The method for water testing according to claim 10, further comprising a step of automatically acquiring multiple images across said targeted sample areas.

12. The method for water testing according to claim 11, further comprising a step of averaging said multiple images across the identified targeted sample areas.

13. The method for water testing according to claim 12, further comprising a step of initiating a flatfield adjustment of the averaged images to account for lighting variations.

14. The method for water testing according to claim 12, further comprising a step of grayscale adjusting the averaged images relative to a reference image.

15. The method for water testing according to claim 9, further comprising a step of completing a RGB to LAB color data conversion.

16. The method for water testing according to claim 15, wherein said step of calculating at said remote computer system analyte parts-per-million (ppm) comprises comparing said adjusted LAB color values to a lookup table to determine analyte ppm.

17. The method for water testing according, to claim 9, further comprising the step of analyzing said calculated analyte ppm to a to determine treatment recommendations and displaying said treatment recommendations to said user in real time.

18. An apparatus for water testing, comprising:
a web-enabled computer having a processor, a computer readable non-transitory storage medium, and software comprising instructions stored on said non-transitory storage medium for receiving a set of colorimetric values corresponding to a test sample, calculating analyte parts-per-million (ppm) from said set of colorimetric values, and outputting said calculated analyte ppm; and a test strip reader comprising a kiosk computer having a user display, a loading shuttle for insertion of a test strip, a lighting assembly for illuminating said inserted test strip, an on-board camera, a processor, a display, and non-transitory storage medium, and software comprising instructions stored on said non-transitory storage medium for providing a user interface on said display to facilitate taking a digital image of said test strip on said loading shuttle of a reagent test strip, for normalizing and analyzing color information in the digital image by colorimetric analysis, and for transmitting a set of colorimetric values corresponding to said digital image to said web-enabled computer for analysis.

19. The apparatus for water testing according to claim 18, further comprising a gas cylinder for ejecting said loading shuttle.

20. The apparatus for water testing according to claim 19, wherein said processor automatically actuates said lighting assembly.

* * * * *